US008784842B2

(12) United States Patent
Davis et al.

(10) Patent No.: US 8,784,842 B2
(45) Date of Patent: Jul. 22, 2014

(54) ALLELIC EXCHANGE MUTAGENESIS IN MAP

(75) Inventors: William C. Davis, Pullman, WA (US); Mary Jo Hamilton, Moscow, ID (US); John Dahl, Pullman, WA (US); Kun Taek Park, Pullman, WA (US)

(73) Assignee: Washington State University, Pullman, WA (US)

( * ) Notice: Subject to any disclaimer, the term of this patent is extended or adjusted under 35 U.S.C. 154(b) by 1114 days.

(21) Appl. No.: 12/668,651

(22) PCT Filed: Jul. 14, 2008

(86) PCT No.: PCT/US2008/069999
§ 371 (c)(1),
(2), (4) Date: Jun. 28, 2010

(87) PCT Pub. No.: WO2009/009798
PCT Pub. Date: Jan. 15, 2009

(65) Prior Publication Data
US 2010/0266627 A1    Oct. 21, 2010

Related U.S. Application Data

(60) Provisional application No. 60/949,504, filed on Jul. 12, 2007.

(51) Int. Cl.
*A61K 39/08* (2006.01)
*C07H 21/02* (2006.01)
*A61K 48/00* (2006.01)

(52) U.S. Cl.
USPC ............... 424/248.1; 424/184.1; 424/185.1; 424/200.1; 424/234.1; 424/93.2; 536/23.1; 536/23.7; 536/24.33

(58) Field of Classification Search
USPC .......... 424/184.1, 185.1, 200.1, 234.1, 248.1, 424/93.2; 536/23.1, 23.7, 24.33
See application file for complete search history.

(56) References Cited

U.S. PATENT DOCUMENTS

| | | | |
|---|---|---|---|
| 6,503,514 B1 | 1/2003 | Flesselles | |
| 7,160,548 B2 | 1/2007 | Gicquel | |
| 2003/0133952 A1* | 7/2003 | Barletta et al. | ............. 424/248.1 |

FOREIGN PATENT DOCUMENTS

WO    WO 01/04267    1/2001

OTHER PUBLICATIONS

Bardarov, S., et al. Microbiology, vol. 148, pp. 3007-3017, 2002.*
U.S. Appl. No. 60/949,504, filed Jul. 12, 2007, Davis.
Aldovini et al., "The uraA Locus and Homologous Recombination in *Mycobacterium bovis* BCG," Journal of Bacteriology, 1993, pp. 7282-7289, vol. 175.

Azad et al., "Targeted replacement of the mycocerosic acid synthase gene in *Mycobacterium bovis* BCG produces a mutant that lacks mycosides," The Proceedings of the National Academy of Sciences, 1996, pp. 4787-4792, vol. 93.
Balasubramanian et al., "Allelic Exchange in *Mycobacterium tuberculosis* with Long

(56) References Cited

OTHER PUBLICATIONS

Cavaignac et al., "Construction and screening of *Mycobacterium paratuberculosis* insertional mutant libraries," Archives of Microbiology, 2000, pp. 229-231, vol. 173.

Chacon et al., "Johne's Disease, Inflammatory Bowel Disease, and *Mycobacterium paratuberculosis*," Annual Review of Microbiology, 2004, pp. 329-363, vol. 58.

Chen et al., "Roles of Lsr2 in Colony Morphology and Biofilm formation of *Mycobacterium smegmatis*," Journal of Bacteriology, 2006, pp. 633-641, vol. 188.

Cox et al., "Complex lipid determines tissue-specific replication of *Mycobacterium tuberculosis* in mice," Nature, 1999, pp. 79-83, vol. 402.

Dahl et al., "The role of $Rel_{Mtb}$-mediated adaptation to stationary phase in long-term persistence of *Mycobacterium tuberculosis* in mice," The Proceedings of the National Academy of Sciences, 2003, pp. 10026-10031, vol. 100.

Foley-Thomas et al., "Phage infection, transfection and transformation of *Mycobacterium avium* complex and *Mycobacterium paratuberculosis*," Microbiology, 1995, pp. 1173-1181, vol. 141.

Harris et al., "Cell Sorting of Formalin-Treated Pathogenic *Mycobacterium paratuberculosis* Expressing GFP," BioTechniques, 2002, pp. 522-527, vol. 32.

Harris et al., "Development of a transposon mutagenesis system for *Mycobacterium avium* subsp. *paratuberculosis*," FEMS Microbiology Letters, 1999, pp. 21-26, vol. 175.

Harris et al., "*Mycobacterium avium* subsp. *paratuberculosis* in Veterinary Medicine," Clinical Microbiology Reviews, 2001, pp. 489-512, vol. 14.

Johnson-Ifearulundu et al., "The effect of subclinical *Mycobacterium paratuberculosis* infection on days open in Michigan, USA, dairy cows," Preventive Veterinary Medicine, 2000, pp. 171-181, vol. 46.

Kalapana et al., "Insertional mutagenesis and illegitimate recombination in mycobacteria," The Proceedings of the National Academy of Sciences, 1991, pp. 5433-5437, vol. 88.

Knipfer et al., "Unmarked Gene Integration into the Chromosome of *Mycobacterium smegmatis* via Precise Replacement of the pyrF Gene," Plasmid, 1997, pp. 129-140, vol. 37.

Krzywinska et al., "*Mycobacterium avium* 104 deleted of the methyltransferase D gene by allelic replacement lacks serotype-secific glycopeptidolipids and shows attenuated virulence in mice," Molecular Microbiology, 2005, pp. 1262-1273, vol. 56.

Li et al., "The complete genome sequence of *Mycobacterium avium* subspecies *paratuberculosis*," The Proceedings of the National Academy of Sciences, 2005, pp. 12344-12349, vol. 102.

McFadden, "Recombination in mycobacteria," Molecular Microbiology, 1996, pp. 20-211, vol. 21.

Otero et al., "Efficient Allelic Exchange and Transposon Mutagenesis in *Mycobacterium avium* by Specialized Transduction," Applied and Environmental Microbiology, 2003, pp. 5039-5044, vol. 69.

Ott et al., "Herd-level economic losses associated with Johne's disease on US dairy operations," Preventive Veterinary Medicine, 1999, pp. 179-192, vol. 40.

Park et al., "Demonstration of Allelic Exchange in the Slow-Growing Bacterium *Mycobacterium avium* subsp. *paratuberculosis*, and Generation of Mutants with Deletions at the pknG, relA, and Isr2 Loci," Applied and Environmental Microbiology, 2008, pp. 1687-1695, vol. 74.

Parker et al., "Expression of the green fluorescent protein (GFP) in *Mycobacterium avium* as a tool to study the interaction between Mycobacteria and host cells," Microbial Pathogenesis, 1997, pp. 193-198, vol. 22.

Pavelka et al., "Comparison of the Construction of Unmarked Deletion Mutations in *Mycobacterium smegmatis*, *Mycobacterium bovis* Bacillus Calmette-Guérin, and *Mycobacterium tuberculosis* H37Rv by Allelic Exchange," Journal of Bacteriology, 1999, pp. 4780-4789, vol. 181.

Sambandamurthy et al., "A pantothenate auxitroph of *Mycobacterium tuberculosis* is highly attenuated and protects mice against tuberculosis," Nature Medicine, 2002, pp. 1171-1174, vol. 8.

Shin et al., "Identification of Novel Virulence Determinants in *Mycobacterium paratuberculosis* by Screening a Library of Insertional Mutants," Infection and Immunity, 2006, pp. 3825-3833, vol. 74.

Shin et al., "Rapid and Reliable Method for Quantification of *Mycobacterium paratuberculosis* by Use of the BACTEC MGIT 960 System," Journal of Clinical Microbiology, 2007, pp. 1941-1948, vol. 45.

Smith et al., "characterization of Auxotrophic Mutants of *Mycobacterium tuberculosis* and Their Potential as Vaccine Candidates," Infection and Immunity, 2001, pp. 1142-1150, vol. 69.

Snapper et al., "Isolation and characterization of efficient plasmic transformation mutants of *Mycobacterium smegmatis*," Molecular Microbiology, 1990, pp. 1911-1919, vol. 4.

Vergne et al., "Mechanism of phagolysosome biogenesis block by viable *Mycobacterium tuberculosis*," The Proceedings of the National Academy of Sciences, 2005, pp. 4033-4038, vol. 102.

Walberger et al., "Protein Kinase G from Pathogenic Mycobacteria Promotes Survival Within Microphages," Science, 2004, pp. 1800-1804, vol. 304.

Weiss et al., "Differential Responses of Bovine Mactophages to *Mycobacterium avium* subsp. *paratuberculosis* and *Mycobacterium avium* subsp. *avium*," Infection and Immunity, 2002, pp. 5556-5561, vol. 70.

* cited by examiner

ALLELIC EXCHANGE MUTAGENESIS IN MAP

CROSS-REFERENCE TO RELATED APPLICATIONS

This application is the U.S. national phase of International Patent Application No. PCT/US2008/06999, filed 14 Jul. 2008, which claims the benefit of priority to U.S. Provisional Patent Application Ser. No. 60/949,504, filed 12 Jul. 2007 and entitled Allelic Exchange Mutagenesis in MAP, which is incorporated herein by reference in its entirety.

STATEMENT REGARDING FEDERALLY-SPONSORED RESEARCH

This work was supported at least in part by the Johne's Disease Integrated Program funded by the Animal Biosecurity program of the USDA-CSREES National Research Initiative 2004-356051-14243, USDA-APHIS 03-9100-0788-GR and 03-9100-07-GR, and Intramural grant USDA Animal Health WNV-00150, and the United States government therefore has certain rights.

SEQUENCE LISTING

A Sequence Listing, comprising SEQ ID NOS:1-49, in both paper (.pdf) and computer readable (.txt) form is included and attached hereto as part of this application.

FIELD OF THE INVENTION

Particular aspects relate generally to wasting disease of the intestine of ruminants, and in particular aspects to Johne's disease, *paratuberculosis* (Ptb), *Mycobacterium avium* subsp. *paratuberculosis* (Map), Crohn's disease, and in particular exemplary aspects to novel and improved and methodologies to generate allelic exchange mutants of slow-growing strains of mycobacteria (e.g., *Mycobacterium avium* subsp. *paratuberculosis* (Map)) to not only provide insight on specific gene function related to virulence, but also to provide for diagnostic assays, and effective vaccines, including live-attenuated Map vaccines and recombinant vaccines for e.g., reducing or precluding shedding during the productive life of dairy cattle. Particular aspects provide novel, non-naturally occurring slow-growing strains of mycobacteria (e.g., Map, *M. bovis*, *M. tuberculosis*) having at least one gene deletion (e.g., pknG, relA, lsr2, panC, panD, proC, trpD, sapM (MAP3432), lysA$_{13}$ 1, leuD, and leuC), vaccines comprising such deletion mutants, or portions thereof, and methods for making said vaccines.

BACKGROUND

Johne's disease, *paratuberculosis* (Ptb), is a chronic wasting disease of the intestine of ruminants caused by *Mycobacterium avium* subsp. *paratuberculosis* (Map). It causes significant economic loss to animal producers, especially in the dairy industry, due to increase in forage consumption, decreased milk production, and early culling due to poor health of affected animals (6, 22, 28). The disease has been difficult to control because of the lack of sensitive specific diagnostic assays and the lack of an efficacious vaccine. Available assays such as Map-antigen ELISAs and the IFN-γ assays vary in their capacity to detect infected animals in the early stages of the disease (36). Available vaccines have been shown to reduce the severity of pathology but not stop shedding of bacteria (18). Consequently, there is a continuing need to develop better diagnostic assays and also a better vaccine that, at a minimum, stops shedding during the productive life of dairy cattle.

An important prerequisite to control this disease is understanding the molecular mechanisms of Map pathogenesis. To increase our knowledge of the genetic basis of virulence and persistence in the host and to develop efficacious potential live vaccines, an efficient method for generating targeted gene knockouts is urgently needed. In contrast to the successful gene disruption in fast-growing mycobacteria such as *M. smegmatis* (8, 10, 24, 33), gene disruption in slow-growing mycobacteria has traditionally proven inefficient, partly due to high frequency of illegitimate recombination and their characteristic aggregation in culture that makes isolation of individual clones problematic (1, 23, 26).

Recent major advances in the methods of genetic manipulation have overcome some of the difficulties encountered in attempting to disrupt genes in slow-growing mycobacteria. The ability to selectively disrupt genes of interest has improved our understanding of pathogenic mycobacterial virulence based on specific gene function. For example, allelic exchange using either linear DNA fragments or suicide vectors, insertion mutagenesis using transposons, and specialized transduction have been successful in *M. tuberculosis* and *M. bovis* (2-4, 7, 11). Although random transposon mutagenesis has been reported in Map (12, 19, 32), directed allelic exchange mutagenesis has still remained intractable. This inability to inactivate specific genes has impeded progress in the use of the recently completed genome sequence of Map K10 (25). A new methodology to generate allelic exchange mutants of Map would provide insight on specific gene function related to their virulence and importantly improve the potential of developing an effective, live-attenuated Map vaccine.

Tuberculosis vaccination. Bacille Calmette-Guérin (BCG), developed in the 1930's, is a vaccine against tuberculosis that is prepared from an attenuated strain of live bovine tuberculosis *bacillus, Mycobacterium bovis*, that has lost its virulence in humans by being specially cultured in an artificial medium for years. BCG is regarded as among the safest and most widely used vaccines in the world, and remains the only vaccination available against tuberculosis. The bacilli have retained enough antigenicity to become a somewhat effective vaccine for the prevention of human tuberculosis. BCG vaccine is at best 80% effective in preventing tuberculosis for a duration of 15 years, however, its protective effect appears to vary according to geography. It is used because it is effective in reducing the likelihood and severity of TB in infants and young children, particularly in areas of the world where TB is highly prevalent, and the chances of exposing an infant or young child are high. In the United States BCG is not used, because TB is not prevalent and the chances are small that infants and young children will become exposed. Additionally, BCG may cause a tuberculin skin test to convert from negative to positive, which is confusing because the TB skin test (Mantoux test) is the best available test for TB infection, and widespread use of BCG would make the skin test less useful.

BCG is efficacious against tuberculous meningitis in the pediatric age group, but its efficacy against pulmonary tuberculosis appears to be variable. The most controversial aspect of BCG is the variable efficacy found in different clinical trials that appears to depend on geography. BCG seems to have its greatest effect in preventing miliary TB or TB meningitis, for which reason, it is still extensively used even in countries where efficacy against pulmonary tuberculosis is negligible. Other recognized uses of BCG include, but are not limited to, use in protecting against leprosy, Buruli ulcer, and in cancer immunotherapy (e.g., superficial forms of bladder cancer, immunotherapy of colorectal cancer, and for the treatment of equine sarcoid in horses), type I diabetes, and interstitial cystitis (IC)/painful bladder syndrome (PBS) (chronic inflammatory bladder problems with unknown etiology). There is, therefore, a pronounced need in the art for novel, and more efficacious compositions and methods for vaccinating against tuberculosis, and other disorders.

Crohn's disease. Crohn's disease (aka regional enteritis) is a chronic, episodic, inflammatory bowel disease (IBD) and is generally classified as an autoimmune disease. The exact cause of Crohn's disease is unknown, but genetic and environmental factors have been invoked in the pathogenesis of the disease. Crohn's disease can affect any part of the gastrointestinal tract from mouth to anus; as a result, the symptoms of Crohn's disease vary among afflicted individuals. The disease is characterized by areas of inflammation with areas of normal lining between in a symptom known as skip lesions. The main gastrointestinal symptoms are abdominal pain, diarrhea (which may be bloody, though this may not be visible to the naked eye), constipation, vomiting, weight loss or weight gain. Crohn's disease can also cause complications outside of the gastrointestinal tract such as skin rashes, arthritis, and inflammation of the eye. Crohn's disease affects between 400,000 and 600,000 people in North America. Prevalence estimates for Northern Europe have ranged from 27-48 per 100,000. Crohn's disease tends to present initially in the teens and twenties, with another peak incidence in the fifties to seventies, although the disease can occur at any age. Although the cause of Crohn's disease is not known, it is believed to be an autoimmune disease that is genetically linked. Unlike the other major types of IBD, there is no cure for Crohn's disease and remission may not be possible or prolonged if achieved. In cases where remission is possible, relapse can be prevented and symptoms controlled with medication, lifestyle changes and in some cases, surgery. Adequately controlled, Crohn's disease may not significantly restrict daily living. Treatment for Crohn's disease is only when symptoms are active and involve first treating the acute problem, then maintaining remission. Treatment options are restricted to controlling symptoms, putting and keeping the disease in remission and preventing relapse.

Interestingly, a recent report by the Canadian Broadcasting Corporation describes an apparent association between *Mycobacterium avium* subsp. *paratuberculosis* (Map) and Crohn's disease, and suggests that transmission of MAP from infected cattle to humans through milk could explain much about the occurrence of Crohn's, including its geographical distribution and rising incidence.

There is, therefore, a pronounced need in the art for novel, and more efficacious compositions and methods for treating and/or preventing Crohn's disease and other inflammatory bowel diseases.

SUMMARY

*Mycobacterium avium* subsp. *paratuberculosis* (Map) disease has been difficult to control because of the lack of an effective vaccine. To address this need, Applicants have developed a novel, efficient allelic exchange method to generate directed mutations within, for example, preselected Map genes.

The present invention is based on the conception that deletion of the gene regions from the genome of virulent mycobacteria (e.g., in slow-growing strains of mycobacteria such as *Mycobacterium avium* subsp. *paratuberculosis* (Map), *M. bovis, M. tuberculosis*) attenuates the virulence of the mycobacteria without eliminating the ability of the mycobacteria to colonize susceptible mammals (e.g., and sustain an infection therein for weeks, months or years). These attenuated mycobacteria are capable of protecting the mammals from challenge by virulent mycobacteria (e.g., Map, *M. bovis, M. tuberculosis*). The attenuated mycobacteria are thus useful in methods and compositions for vaccination of humans, cows and other mammals from virulent mycobacteria.

Particular exemplary aspects provide, for the first time, an efficient allelic exchange mutagenesis system in slow growing mycobacteria, such as *Mycobacterium avium* subsp. *paratuberculosis* (Map), *M. bovis*, and *M. tuberculosis* and generation of deletion mutants at various exemplary loci (e.g., pknG, relA and lsr2 loci).

Particular exemplary aspects provide an efficient allelic exchange mutagenesis system in Map K10 (AE016958; gi: 41400296), a clinical isolate and the strain chosen for the Map genome sequencing project (13, 17, 25), using a phage-delivery system Particular aspects provide a method for directed allelic exchange mutagenesis of slow-growing *mycobacterium* (sp), comprising: providing a conditionally replicating transducing mycobacteriophage containing an allelic exchange substrate (AES), the AES comprising a selectable gene flanked by upstream and downstream homologous regions that flank a target locus or gene; culturing a slow-growing mycobacteria strain characterized by clumping during culturing, followed by gravity sedimentation, low-speed centrifugation to provide a low-speed mycobacteria pellet, and resuspension of the low-speed mycobacteria pellet in culture medium suitable for transducing; culturing the resuspended slow-growing mycobacteria strain in the presence of the transducing mycobacteriophage at a non-permissive temperature; depleting bacterial clumps by vigorously shaking the cultures, followed low-speed centrifugation to provide a low-speed mycobacteria pellet, and resuspending of the low-speed mycobacteria pellet in a culture medium or buffer; withdrawing an amount of the resuspension; and selecting, using the withdrawn amount and a suitable selection medium, allelic exchange mutants of the slow-growing mycobacteria strain.

In certain aspects, the slow-growing strain of mycobacteria is *Mycobacterium avium* subsp. *paratuberculosis* (Map), Map K10, *Mycobacterium bovis*, or *Mycobacterium tuberculosis*. In particular embodiments, the selectable gene is hygromycin resistant ($Hyg^R$). In certain implementations, the selectable gene is flanked by site-specific resolvase sites. In particular aspects, the selection medium comprises at least 75 μg/ml hygromycin.

In certain preferred aspects, the method comprises culturing of the slow-growing strain of mycobacteria strain in a medium containing a nonionic surfactant and/or emulsifier, followed by washing the cultured mycobacteria to remove the nonionic surfactant and/or emulsifier prior to culturing in the presence of the transducing mycobacteriophage. In certain aspects, the nonionic surfactant and/or emulsifier comprises polysorbate 80.

In particular embodiments, the target gene is at least one selected from the group of genes consisting of pknG, relA, lsr2, panC, panD, proC, trpD, sapM (MAP3432), lysA_1, leuD, and leuC. In certain preferred embodiments, the allelic exchange frequency is a least 75% for a transduction frequency of $9.5 \times 10^{-8}$ to $1.6 \times 10^{-7}$.

In particular embodiments, the method further comprises confirmation of the allelic exchange mutants using at least one of polymerase chain reaction (PCR), nucleic acid sequencing, and RNA expression analysis.

Additional aspects provide method for preparing a vaccine composition, comprising: obtaining an allelic exchange mutant of a slow-growing strain of mycobacteria derived by a method according to any one of claims 1 through 10; and generating a vaccine using the allelic exchange mutant, or a portion thereof. In certain aspects, deriving the vaccine comprises use of the allelic exchange mutant, or the portion thereof, to prepare a recombinant *Mycobacterium avium* subsp. *paratuberculosis*, *M. bovis* or *M. bovis* Bacille Calmette-Guérin (BCG), or *M. tuberculosis*-based vaccine.

In certain preferred embodiments, the vaccine comprises a live-attenuated vaccine.

Additional aspects provide a vaccine composition comprising a non-naturally occurring mycobacteria mutant prepared by the inventive methods, or a portion of said mutant, in a pharmaceutically acceptable carrier or excipient, wherein the vaccine is suitable to protect a mammal from challenge by a virulent *mycobacterium*. In certain aspects, the virulent mycobacterium is *Mycobacterium avium* subsp. *paratuberculosis* (Map), *M. bovis*, or *M. tuberculosis*. In particular aspects, the mammal is a cow, human, or human child. In certain embodiments, the slow-growing strain of mycobacteria is *Mycobacterium avium* subsp. *paratuberculosis* (Map), Map K10, *Mycobacterium bovis*, or *Mycobacterium tuberculosis*. In certain aspects, the slow-growing strain of mycobacteria is *Mycobacterium avium* subsp. *paratuberculosis* (Map), and the target gene is at least one selected from the group consisting of pknG, relA, lsr2, panC, panD, proC, trpD, sapM (MAP3432), lysA_1, leuD, and leuC. In particular embodiments, the pknG, relA, lsr2, panC, panD, proC, trpD, sapM (MAP3432), lysA_1, leuD, and leuC genes comprise SEQ ID NOS:1, 4, 6, 34, 36, 38, 40, 42, 44, 46 and 48, contiguous portions thereof, or sequences at least 95%, at least 98%, or at least 99% identical thereto, respectively. In preferred aspects, the vaccine comprises a live-attenuated vaccine.

In additional aspects, the non-naturally occurring mycobacteria mutant strain further comprises a foreign DNA stably integrated its genomic DNA. In certain aspects, the foreign DNA encodes at least one protein or polypeptide selected from the group consisting of an antigen, an enzyme, a lymphokine, an immunopotentiator, and a reporter molecule. In particular embodiments, the foreign DNA encodes at least one protein antigen selected from the group consisting of antigens from *Mycobacterium leprae*, *Mycobacterium tuberculosis*, malaria sporozoites, malaria merozoites, diphtheria toxoid, tetanus toxoids, *Leishmania* spp., *Salmonella* spp., *Mycobacterium africanum*, *Mycobacterium intracellulare*, *Mycobacterium avium*, *Treponema* spp., Pertussis, Herpes virus, Measles virus, Mumps virus, *Shigella* spp., *Neisseria* spp., *Borrelia* spp., rabies, polio virus, Human immunodeficiency virus, snake venom, insect venom, and *Vibrio cholera*; steroid enzymes; interleukins; tumor necrosis factor alpha and beta; interferon alpha, beta, and gamma; and reporter molecules GFP, luciferase, beta-galactosidase, beta-glucuronidase and catechol dehydrogenase. In certain aspects, the vaccine is for at least one of Johne's disease, *paratuberculosis* (Ptb), Crohn's disease, and tuberculosis.

Further aspects provide a non-naturally occurring allelic exchange mutant of a slow-growing strain of mycobacteria derived by a method according to the inventive methods. In particular aspects, the slow-growing strain of mycobacteria is *Mycobacterium avium*, *Mycobacterium avium* subsp. *paratuberculosis* (Map), Map K10, *Mycobacterium bovis*, or *Mycobacterium tuberculosis*. In certain embodiments, the *Mycobacterium avium* subsp. *paratuberculosis* (Map) is a GFP-expressing strain of Map K-10. In particular implementations, the slow-growing strain of mycobacteria is *Mycobacterium avium* subsp. *paratuberculosis* (Map), and the target gene is at least one selected from the group consisting of pknG, relA, lsr2, panC, panD, proC, trpD, sapM (MAP3432), lysA_1, leuD, and leuC.

Yet further embodiments provide a non-naturally occurring deletion mutant of *Mycobacterium avium* subsp. *paratuberculosis* (Map), wherein the Map exhibits attenuated virulence in a mammal when compared to the Map without the deletion. In particular aspects, the deletion mutant is derived by the inventive methods. In particular aspects, the target gene is at least one selected from the group consisting of pknG, relA, lsr2, panC, panD, proC, trpD, sapM (MAP3432), lysA_1, leuD, and leuC. In certain embodiments, the pknG, relA, lsr2, panC, panD, proC, trpD, sapM (MAP3432), lysA_1, leuD, and leuC genes comprise SEQ ID NOS:1, 4, 6, 34, 36, 38, 40, 42, 44, 46 and 48, contiguous portions thereof, or sequences at least 95%, at least 98%, or at least 99% identical thereto, respectively.

Additional aspects provide a method of protecting a mammal from a virulent *Mycobacterium avium* subsp. *paratuberculosis* (Map), *M. bovis*, or *M. tuberculosis*, comprising treating the mammal with the vaccine based on the non-naturally occurring deletion mutant disclosed herein. In particular aspects, the vaccine is administered subcutaneously or intradermally.

Further aspects provide methods of protecting a mammal from a virulent *Mycobacterium avium* subsp. *paratuberculosis* (Map), *M. bovis*, or *M. tuberculosis*, comprising treating the mammal with the inventive vaccines.

DETAILED DESCRIPTION

Figure 1:
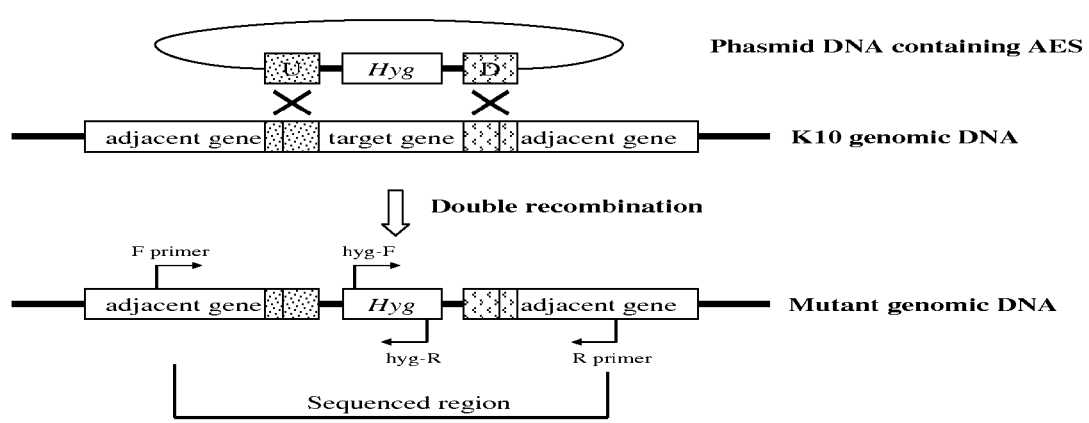
FIG. 1 shows, according to particular exemplary aspects, a schematic representation of allelic exchange mutagenesis in Map. The inserted sequence containing the Hyg gene are of identical size in all mutants (1,915-bp), but deleted sequence sizes vary according to mutants in this study (see Table 2). Arrows indicate schematic binding sites and directions of primers used for PCR identification. F and R primers represent the primers designed to bind outside of up- and downstream homologous regions in each mutant. PCR was performed with a combination of primers (F and R primers, F primer and hyg-R, or hyg-F and R primer). Hyg, hygromycin-resistant gene; U and D, up- and downstream homologous regions.

*Mycobacterium avium* subsp. *paratuberculosis* (Map) disease has been difficult to control because of the lack of an effective vaccine. To address this need, Applicants have developed a novel, efficient allelic exchange method to generate directed mutations within preselected Map genes.

Particular exemplary aspects provide, for the first time, an efficient allelic exchange mutagenesis system in slow growing *Mycobacterium* (e.g., demonstration of allelic exchange in the slow growing *Mycobacterium avium* subsp. *paratuberculosis* and generation of deletion mutants at the pnkG, relA and lsr2 loci. According to further aspects, other exemplary loci include, but are not limited to panC, panD, proC, trpD, sapM (MAP3432), lysA_1, leuD, and leuC.

Particular exemplary aspects provide an efficient allelic exchange mutagenesis system in Map K10 (AE016958; gi: 41400296), a clinical isolate and the strain chosen for the Map genome sequencing project (13, 17, 25), using a phage-delivery system. To demonstrate the efficiency of this phage-based tool for generating a targeted gene disruption in the isogenic strain, the orthologues of two known virulence genes in pathogenic mycobacteria (relA (SEQ ID NOS:4 and 5), and pknG (SEQ ID NO:1 (This sequence is a complementary sequence, which is shown as a reverse complemented sequence of actual coding sequence) and SEQ ID NO:2) (16, 34) and one gene related to colony morphology and biofilm formation in fast growing mycobacteria (lsr2 (SEQ ID NOS:6 and 7)) (14) were successfully disrupted with high efficiency in Map K10. In addition, since GFP is widely used as a molecular tool for characterization of microbial pathogenesis, Applicants also made these three gene deletions in GFP-tagged Map K10 (Map K10-GFP (AE016958; gi: 41400296); (20) to facilitate study of specific gene function in cells and tissue.

Aspects of the present invention provide an efficient allelic exchange system in Map and provide a foundational technology that can be used to elucidate specific gene function and develop vaccine, including but not limited to novel live attenuated vaccines.

With the disclosed novel Method B, described herein, the allelic exchange frequency was 78-100% for a transduction frequency of $9.5 \times 10^{-8} - 1.6 \times 10^{-7}$. Three exemplary Map genes were selected for mutagenesis: pknG and relA, genes known to be important virulence factors in mycobacteria and lsr2, a gene regulating lipid biosynthesis. These mutants were additionally successfully generated using Applicants' Method B in the sequencing project virulent strain K10 and in a recombinant strain expressing the green fluorescent protein gene, gfp. The improved efficiency of disrupting selected genes in Map provides for accelerated development of additional mutants for vaccine production and functional studies.

The present invention is based on the conception that deletion of the gene regions from the genome of virulent mycobacteria (e.g., in slow-growing strains of mycobacteria such as *Mycobacterium avium* subsp. *paratuberculosis* (Map), *M. bovis, M. tuberculosis*) attenuates the virulence of the mycobacteria without eliminating the ability of the mycobacteria to sustain viability and colonize susceptible mammals (e.g., and sustain an infection therein for weeks, months or years). These attenuated mycobacteria are capable of protecting the mammals from challenge by virulent mycobacteria (e.g., Map, *M. bovis, M. tuberculosis*). The attenuated mycobacteria are thus useful in methods and compositions for vaccination of humans, cows and other mammals from virulent mycobacteria.

Thus, in some embodiments, the invention is directed to non-naturally occurring slow-growing strains of mycobacteria, such as *Mycobacterium avium* subsp. *paratuberculosis* (Map), *M. bovis*, and *M. tuberculosis*, that comprise at least one deletion (e.g., deletions of/in pknG, relA, lsr2, panC, panD, proC, trpD, sapM (MAP3432), lysA_1, leuD, and leuC). These slow-growing strains of mycobacteria preferably exhibit attenuated virulence in a mammal when compared to the corresponding strain without the deletion.

A host organism can be inoculated with the mycobacteria of the present invention by any of a number of ways known in the art. These include oral ingestion, gastric intubation, or broncho-nasal-ocular spraying. Other methods of administration include intravenous, intramuscular, intramammary, or, preferably, subcutaneous or intradermal injection. The immunization dosages required can be determined without undue experimentation. One or two dosages of avirulent mycobacteria at $1\text{-}2 \times 10^6$ colony forming units (CFU) have previously been used, but other dosages are contemplated within the scope of the invention. Multiple dosages can be used as needed to provide the desired level of protection from challenge.

It is well known in the art that in order to elicit an immune response with a live vaccine such as an avirulent *mycobacterium*, it is preferred that the vaccine organism can sustain an infection in the immunized host, to provide a sustained exposure of the host's immune system to the organism. Therefore, in various preferred embodiments, the non-naturally occurring, slow-growing strains of mycobacteria, such as *Mycobacterium avium* subsp. *paratuberculosis* (Map), *M. bovis*, and *M. tuberculosis*, that comprise at least one deletion (e.g., deletions of/in pknG, relA, lsr2, panC, panD, proC, trpD, sapM (MAP3432), lysA_1, leuD, and leuC) of the invention are capable of sustaining an infection in the host. The ability to sustain infection can be measured without undue experimentation by any of a number of ways described in the art. With the *mycobacterium* of the present invention, a preferred way of measuring sustained infection is by determining whether viable mycobacteria of the inoculated strain will remain resident in an immunocompetent mammal (e.g., mouse, cow, etc.), or cells derived therefrom, for a sustained period (e.g., more than four weeks). More preferably, the inoculated mycobacteria will remain resident in the mammal or cells derived therefrom for at least ten weeks. In the most preferred embodiments, viable mycobacteria of the inoculated strain will remain resident in the in the mammal or cells derived therefrom for at least 20 weeks.

Preferably, the attenuated mycobacteria of the invention are capable of protecting a mammal from challenge by a virulent slow-growing strain of mycobacteria, such as *Mycobacterium avium* subsp. *paratuberculosis* (Map), *M. bovis*, and *M. tuberculosis*. This ability can be determined by any of a number of ways provided in the literature. A preferred method is delivering the virulent mycobacteria to an immunocompetent mammal. Preferably, the delivery closely mimics natural infection. The skilled artisan would understand that the ability of an avirulent *mycobacterium* to protect the mammal from challenge from a virulent *mycobacterium* is indicative of the ability of the avirulent *mycobacterium* to protect a human, including a human child, from infection (e.g., by Map, *M. bovis*, and *M. tuberculosis*). A more stringent test of an avirulent *mycobacterium* to prevent infection by a virulent challenge is to use an immunocompromised mammal if available (e.g., a SCID mouse).

The deletion of at least one gene (e.g., deletions of/in pknG, relA, lsr2, panC, panD, proC, trpD, sapM (MAP3432), lysA_1, leuD, and leuC) is contemplated in these embodiments with any slow-growing strain of mycobacteria, such as *Mycobacterium avium* subsp. *paratuberculosis* (Map), *M. bovis*, and *M. tuberculosis*. Preferably, the strain is a virulent strain, since those strains would be most likely to sustain an infection after the deletion is made. Preferred strains are Map, Map K-10, or a GFP-expressing strain of Map K-10.

In some aspects of these embodiments, the deletion is of at least one of pknG, relA, lsr2, panC, panD, proC, trpD, sapM (MAP3432), lysA_1, leuD, and leuC. Strains with these deletions can be determined by any means in the art, preferably by molecular genetic means, for example by hybridization methods (e.g., Southern blot using respective probes from these regions) or by amplification methods (e.g., PCR using primers to amplify a portion of the respective regions). Examples of Map deletion target regions of pknG, relA, lsr2, panC, panD, proC, trpD, sapM (MAP3432), lysA_1, leuD, and leuC are provided herein as SEQ ID NOS:1, 4, 6, 34, 36, 38, 40, 42, 44, 46 and 48, contiguous portions thereof, or sequences at least 95%, at least 98%, or at least 99% identical thereto, respectively. The skilled artisan could identify additional or analogous regions from other slow-growing strains of mycobacteria, such as *M. bovis*, and *M. tuberculosis* without undue experimentation. Those orthologous regions would be expected to have strong homology to the exemplary SEQ ID NOS given above (e.g., at least 85%, at least 90%, at least 95%, at least 97%, at least 98% or at least 99% homologous to the exemplary SEQ ID NOS given above. However, it is to be understood that virulent mycobacteria can be rendered avirulent by deletions in a portion of these exemplary gene regions. Therefore, non-naturally occurring Map, *M. bovis*, and *M. tuberculosis* that have a partial deletion in such exemplary genes or regions are envisioned as within the scope of the invention, provided the deletion can cause a virulent *M. tuberculosis* to become avirulent. It is expected that such slow-growing strains of mycobacteria (e.g., Map, *M. bovis*, and *M. tuberculosis*) with partial deletions can still sustain an infection in a mammal and protect against challenge by a virulent mycobacteria.

In embodiments where the deletion is in a region controlling production of a vitamin or amino acid, the deletion can be in any genetic element leading to loss of production of the vitamin or amino acid, including structural genes for enzymes involved in the biosynthesis of the vitamin or amino acid and genetic control elements such as promoters, enhancers, etc.

Deletion of a region controlling production of any essential vitamin, or amino acid, or their precursors is contemplated as within the scope of the invention. As used herein, an essential vitamin is defined by its normal usage, that is, a small molecular weight compound that is required as a cofactor for the efficient function of an essential enzyme or enzymes. Non-limiting examples include vitamin A, thiamin (BI), riboflavin (B2), nicotinic acid (niacin)/nicotinamide/nicotinamide adenine dinucleotide (NAD)/nicotinamide adenine dinucleotide phosphate (NADP/coenzyme II), pantothenate (pantothenic acid/B5), pyridoxine (B6), folic acid, B12, biotin, C, D, E and K. Preferred vitamin targets for deletion include nicotinamide and pantothenate. Methods for determining whether a *mycobacterium* has deletions leading to the loss of production of any of these vitamins are within the scope of the art. Deletions leading to the loss of any of these vitamins or amino acids would be expected to lead to attenuated virulence of an otherwise virulent *mycobacterium*. Any of those strains would also be expected to sustain an infection in a mammal. Preferred vitamin targets are pantothenate and nicotinamide adenine dinucleotide (NAD). A preferred pantothenate deletion is of structural genes in the pantothenate biosynthetic operon, most preferably the panC and panD genes, the combined mutation being delta-panCD. An example of a deletion of those genes is the deletion of the sequence from a slow-growing strain of mycobacteria (e.g., Map, *M. bovis*, and *M. tuberculosis*) provided herein as SEQ ID NOS:36 and 38, or deletion of a portion of either or both of these sequences. Similarly, a preferred NAD deletion is in the structural genes of the NAD biosynthetic operon, most preferably the nad B and C genes, the combined mutation being delta-nadBC.

In similar embodiments, the invention is directed to any of the above-described slow-growing strains of mycobacteria (e.g., Map, *M. bovis*, and *M. tuberculosis*) that are produced by deleting a target gene region or a region controlling production of the target gene. The deletion can be made by serial in vitro passage of virulent mycobacteria (as the well-known *M. bovis* BCG was made) and selection for the desired deletion. More preferably, however, the deletion is made by genetic engineering, since such genetic methods allow precise control of the deletion being made. Various methods of making deletions in mycobacteria are known in the art. Non-limiting examples include specialized transduction (see, e.g., U.S. Pat. No. 6,271,034, incorporated herein), and sequential two-step recombination with selectable markers.

Since, in preferred embodiments of the invention, the slow-growing strains of mycobacteria (e.g., Map, *M. bovis*, and *M. tuberculosis*) exhibit attenuated virulence and can sustain an infection in a mammal, these mycobacteria can usefully further employ a foreign DNA stably integrated into the genome of the mycobacteria, such that the mycobacteria can express a gene product coded by the foreign DNA (see, e.g., U.S. Pat. No. 5,504,005 incorporated herein). Thus, it is apparent that the present invention has wide applicability to the development of effective recombinant vaccines against bacterial, fungal, parasite or viral disease agents in which local immunity is important and might be a first line of defense. Non-limiting examples are recombinant vaccines for the control of bubonic plague caused by *Yersinia pestis*, of gonorrhea caused by *Neisseria gonorrhoea*, of syphilis caused by *Treponema pallidum*, and of venereal diseases or eye infections caused by *Chlamydia trachomatis*. Species of *Streptococcus* from both group A and group B, such as those species that cause sore throat or heart disease, *Neisseria meningitidis, Mycoplasma pneumoniae, Haemophilus influenzae, Bordetella pertussis, Mycobacterium leprae, Streptococcus pneumoniae, Brucella abortus, Vibrio cholerae, Shigella* spp., *Legionella pneumophila, Borrelia burgdorferi, Rickettsia* spp., *Pseudomonas aeruginosa*, and pathogenic *E. coli* such as ETEC, EPEC, UTEC, EHEC, and EIEC strains are additional examples of microbes within the scope of this invention from which foreign genes could be obtained for insertion into mycobacteria of the invention. Recombinant anti-viral vaccines, such as those produced against influenza viruses, are also encompassed by this invention. Recombinant anti-viral vaccines can also be produced against viruses, including RNA viruses such as Picornaviridae, Caliciviridae, Togaviridae, Flaviviridae, Coronaviridae, Rhabdoviridae, Filoviridae, Paramyxoviridae, Orthomyxoviridae, Bunyaviridae, Arenaviridae, Reoviridae or Retroviridae; or DNA viruses such as Hepadnaviridae, Paroviridae, Papovaviridae, Adenoviridae, Herpesviridae or Poxyiridae. Recombinant vaccines to protect against infection by pathogenic fungi, protozoa or parasites are also contemplated by this invention.

The avirulent microbes of the present invention are also contemplated for use to deliver and produce foreign genes that encode pharmacologically active products that might stimulate or suppress various physiological functions (i.e., growth rate, blood pressure, etc.). In such microbes, the recombinant gene encodes said pharmacologically active products.

By immunogenic agent is meant an agent used to stimulate the immune system of an individual, so that one or more functions of the immune system are increased and directed towards the immunogenic agent. Immunogenic agents include vaccines. An antigen or immunogen is intended to mean a molecule containing one or more epitopes that can stimulate a host immune system to make a secretory, humoral and/or cellular immune response specific to that antigen.

In preferred embodiments, the foreign DNA encodes an antigen, an enzyme, a lymphokine, an immunopotentiator, or a reporter molecule. Preferred examples include antigens from *Mycobacterium leprae*, *Mycobacterium tuberculosis*, malaria sporozoites, malaria merozoites, diphtheria toxoid, tetanus toxoids, *Leishmania* spp., *Salmonella* spp., *Mycobacterium africanum*, *Mycobacterium intracellulare*, *Mycobacterium avium*, *Treponema* spp., Pertussis, Herpes virus, Measles virus, Mumps virus, *Shigella* spp., *Neisseria* spp., *Borrelia* spp., rabies, polio virus, human immunodeficiency virus, snake venom, insect venom, and vibrio cholera ; steroid enzymes; interleukins (e.g., 1-10); tumor necrosis factor alpha and beta; interferon alpha, beta and gamma; and reporter molecules GFP, luciferase, beta-galactosidase, beta-glucuronidase and catechol dehydrogenase.

In additional embodiments, the invention is directed to Johne's disease, *paratuberculosis* (Ptb), Crohn's disease, and tuberculosis vaccines made using any of the above described mycobacteria, in a pharmaceutically acceptable excipient. These vaccines are capable of protecting the mammal from challenge by virulent mycobacteria. In some preferred embodiments, the *mycobacterium* is Map, or *M. bovis* and the mammal is a cow; in other preferred embodiments, the *mycobacterium* is *M. tuberculosis* and the mammal is a human (e.g., a human child).

By vaccine is meant an agent used to stimulate the immune system of an individual so that protection is provided against an antigen not recognized as a self-antigen by the immune system. Immunization refers to the process of inducing a continuing high level of antibody and/or cellular immune response in which T-lymphocytes can either kill the pathogen and/or activate other cells (e.g., phagocytes) to do so in an individual, which is directed against a pathogen or antigen to which the organism has been previously exposed. The phrase "immune system" refers herein to the anatomical features and mechanisms by which a mammal produces antibodies against an antigenic material which invades the cells of the individual or the extra-cellular fluid of the individual and is also intended to include cellular immune responses. In the case of antibody production, the antibody so produced can belong to any of the immunological classes, such as immunoglobulins, A, D, E, G or M, and additionally encompass antigen binding fragments or derivatives thereof. Immune responses to antigens are well studied and widely reported. A survey of immunology is provided in Elgert (1996) and Stites et al. (1991).

The pharmaceutical carrier or excipient in which the vaccine is suspended or dissolved may be any solvent or solid or encapsulating material. The carrier is non-toxic to the inoculated individual and compatible with the microorganism or antigenic gene product. Suitable pharmaceutical carriers are known in the art and, for example, include liquid carriers, such as normal saline and other non-toxic salts at or near physiological concentrations, and solid carriers, such as talc or sucrose. Gelatin capsules can serve as carriers for lyophilized vaccines. Adjuvants may be added to enhance the antigenicity if desired. When used for administering via the bronchial tubes, the vaccine is preferably presented in the form of an aerosol. Suitable pharmaceutical carriers and adjuvants and the preparation of dosage forms are described in, for example, Gennaro (1985).

Similarly, the invention is directed to methods of protecting a mammal from a virulent *mycobacterium* (e.g., Map, *M. bovis*, *M. tuberculosis*). The methods comprise treating the mammal with any of the above-described vaccines. The vaccines can be administered by oral ingestion, gastric intubation, or broncho-nasal-ocular spraying, intravenous, intramuscular, intramammary, or, preferably, by subcutaneous or intradermal injection. The immunization dosages required can be determined without undue experimentation. One or two dosages of avirulent mycobacteria at $1\text{-}2\times10^6$ colony forming units (CFU) have previously been used, but other dosages are contemplated within the scope of the invention. Multiple dosages can be used as needed to provide the desired level of protection from challenge.

The present invention is also directed to methods of preparing a vaccine. The methods comprise deleting at least one gene region as described herein, or a region controlling production of a gene product in a slow-growing strain of mycobacteria (e.g., Map, *M. bovis*, *M. tuberculosis*) to produce any of the mycobacteria described.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

In accordance with the present invention there may be employed conventional molecular biology, microbiology, and recombinant DNA techniques within the skill of the art. Such techniques are explained fully in the literature (see, e.g., Maniatis, Fritsch & Sambrook, "Molecular Cloning: A Laboratory Manual" (1989 or later addition); "Current Protocols in Molecular Biology" Volumes I-IV (Ausubel, R. M., ed. (1997); and "Cell Biology: A Laboratory Handbook" Volumes I-III (J. E. Celis, ed. (1994).

Rationale Design and Construction of Attenuated Mutants as Vaccines, and Treatment of *Mycobacteria*-related Diseases Including Map-related Diseases:

The ability to obtain directed gene knockouts in Map is a major breakthrough in Johne's disease research. Results from sequencing the Map K10 genome (accession number (AE016958; NC_002944) have shown identified 4350 annotated genes, where many of these represent orthologs of known *mycobacterium* genes, but where 41.6% of these annotated genes are unknown or hypothetical ORFs (25). Only through specific gene disruptions, can potential phenotypes be assigned to these unknown genes. Additionally, the disclosed methods now provide for rationale design and construction of attenuated mutants as vaccines. Persistence within host macrophages is a key feature of mycobacterial pathogenesis that needs to be further understood. By selectively disrupting Map genes, e.g., pknG and relA by allelic exchange, the present Applicants have taken a foundational step in this direction as both pknG and relA have been shown to be key virulence determinants in *M. tuberculosis* and *M. bovis* (16, 34). The ability to selectively disrupt genes in *M. tuberculosis* has already facilitated advancement of knowledge of specific gene functions in *M. tuberculosis* (2, 3, 7, 11, 15, 30).

Johne's disease. In particular aspects, the present invention provides methods and compositions for the generation of Map vaccines for protecting against Johne's disease in cattle.

Crohn's disease, tuberculosis, and other diseases. As mentioned above, a recent report by the Canadian Broadcasting Corporation describes an apparent association between *Mycobacterium avium* subsp. *paratuberculosis* (Map) and Crohn's disease, and suggests that transmission of MAP from infected cattle to humans through milk could explain much about the occurrence of Crohn's, including its geographical distribution and rising incidence.

In particular aspects, the present invention provides methods and compositions for the generation of Map vaccines for protecting against Crohn's disease and tuberculosis in humans. Moreover, the compositions can be used to generate recombinant vaccines based on BCG, *M. bovis* and *M. tuberculosis*. Other recognized uses of BCG include, but are not limited to, use in protecting against leprosy, Buruli ulcer, and in cancer immunotherapy (e.g., superficial forms of bladder cancer, immunotherapy of colorectal cancer, and for the treatment of equine sarcoid in horses), type I diabetes, and interstitial cystitis (IC)/painful bladder syndrome (PBS) (chronic inflammatory bladder problems with unknown etiology).

Disruption of pknG and relA in *M. Avium* Subsp. *Paratuberculosis* (Map).

Allelic exchange mutagenesis using specialized transduction has been used successfully in some slow growing mycobacteria, including *M. tuberculosis, M. bovis* and *M. avium* (4, 27). However, successful use of the technology has not been previously reported in Map. Applicants have improved and extended this approach to develop, or the first time, efficient targeted gene disruptions in Map, one of the slowest growing mycobacterial species with a generation time (24 h or longer) that is at least 1½ times longer than that of *M. tuberculosis* (31).

Example 2, herein below, describes disruption of pknG and relA in *M. avium* subsp. *paratuberculosis*. In the first trial (Method A), which was similar to a previous study of *M. tuberculosis* and *M. bovis* BCG (4), Applicants experienced a high rate of spontaneous Hyg$^R$ or illegitimate recombination. A previous study with *M. avium* produced similar results (27). To overcome the very low efficiency of allelic exchange in that study, those authors used a leuD deletion mutant of *M. avium* as a genetic host with *Streptomyces clelicolor* ledD gene as a selective marker.

In contrast, as described in Example 3, using the present Applicants' disclosed Method B, the present Applicants have achieved herein a high efficiency of allelic exchange in Map (up to 100% of allelic exchange frequency and 1.6×10$^{-7}$ of transduction frequency; TABLE 3). Importantly, the successful development of this method allows this tool to be used routinely to generate directed gene deletions in an isogenic virulent strain of Map.

Applicants additionally disrupted the Map lsr2 gene using Method B as described in Example 3 herein below.

The non-naturally occurring Map pknG, relA and lsr2 mutants disclosed herein are novel, and represent first allelic exchange mutants in these Map loci.

Applicants, as described in Example 3, have determined, unexpectedly, that removal of clumped bacteria by using gravity sedimentation, preferably, using consecutive gravity sedimentations, allows for very efficient allelic exchange using Method B. While other mechanical methods might be used to disrupt cell clumps, such as passing through a syringe or sonication, Applicants speculated that these physical disruptions might cause damage to the cells, which may in turn decrease the viability of transduced bacteria on Hyg-containing medium. In addition, by combining the use of gravity sedimentation with increasing the concentration of Hyg to 75 µg/ml (e.g., or greater) the rate of spontaneous Hyg$^R$ was greatly diminished. When only 50 µg/ml Hyg was used, as typical in the art, many spontaneous Hyg$^R$ were generated in the experiments for *M. avium* (27) and for Map (TABLE 3). In contrast, use of 75 µg/ml Hyg showed an excellent selective pressure for isolating mutant colonies of *M. tuberculosis, M. bovis* (4), and Map in this study (TABLE 3). All transduction frequencies in Method B, except for ΔrelAL in Map K10, were calculated around 10$^{-7}$ per recipient cells, which were similar to previous studies for transposon mutagenesis for Map by specialized transduction (19). However, Applicants estimated the number of cells at OD$_{600}$ between 0.6 and 0.8 as 6×10$^8$ CFU/ml based on the results of CFU counting in Applicants' lab, while other studies of transposon mutagenesis for Map interpreted the same OD value as 1.5 to 2.0×10$^8$ CFU/ml (12, 19, 32). If Applicants used this number for recipient cells (2.0×10$^8$ CFU/ml), the calculated transduction frequencies in this study would increase three times. Contrary to the previous finding for *M. bovis* BCG (4), the recovery time for transduced Map by specialized transducing mycobacteriophage did not show much effect on the allelic exchange frequency in the current study (TABLE 4). This indicates that the recovery time is not a critical factor for achieving a high efficiency of allelic exchange Example 4 herein discloses additional exemplary preferred Map loci for efficient allelic exchange mutagenesis. The complete genomic sequence of *Mycobacterium avium* subsp. *paratuberculosis* K-10, is currently known (see accession number AE016958; gi:41400296), and 4,350 protein encoding loci have been currently identified. Applicants' invention provides, for the first time, an efficient system for generating allelic exchange mutants in *Mycobacterium avium* subsp. *Paratuberculosis* (Map), including in Map K-10. According to additional aspects, the presently disclosed methods can be used to target any of the 4350 known protein encoding loci in Map K-10, or any known loci in Map or any other slow-growing *mycobacterium*. TABLE 5 of Example 4, for example, lists (in addition to PknG, Re1A and Lsr2, discussed above) other preferred, exemplary genes for which allelic exchange mutants can be generated using the disclosed inventive methods. Such target include, but are not limited to, pknG, relA, lsr2, panC, panD, proC, trpD, sapM (MAP3432), lysA_1, leuD , leuC, etc. In further aspects, the *M. avium* homolog of the pcaA gene, recognized in the art as being important for *M. tuberculosis* pathogenesis, is targeted by the inventive methods. Genes for vitamin production, or amino acid production comprise additional exemplary targets.

An additional novel benefit in present study, as shown in Example 5 herein, is the ability to create defined mutants in a GFP-expressing strain of Map K-10. According to additional aspects, this feature enable easy tracking of mutants in a variety of downstream assays, including infection of macrophages as shown in this study (see, e.g., FIG. 4). Applicants have demonstrated that the efficiencies of allelic exchange in Map K10-GFP were similar to those of wild type Map K-10 (TABLES 3 and 4) and some of those mutants still expressed GFP with various percentages after lengthy incubation without selective pressure for the GFP plasmid (TABLE 6).

Figure 4:
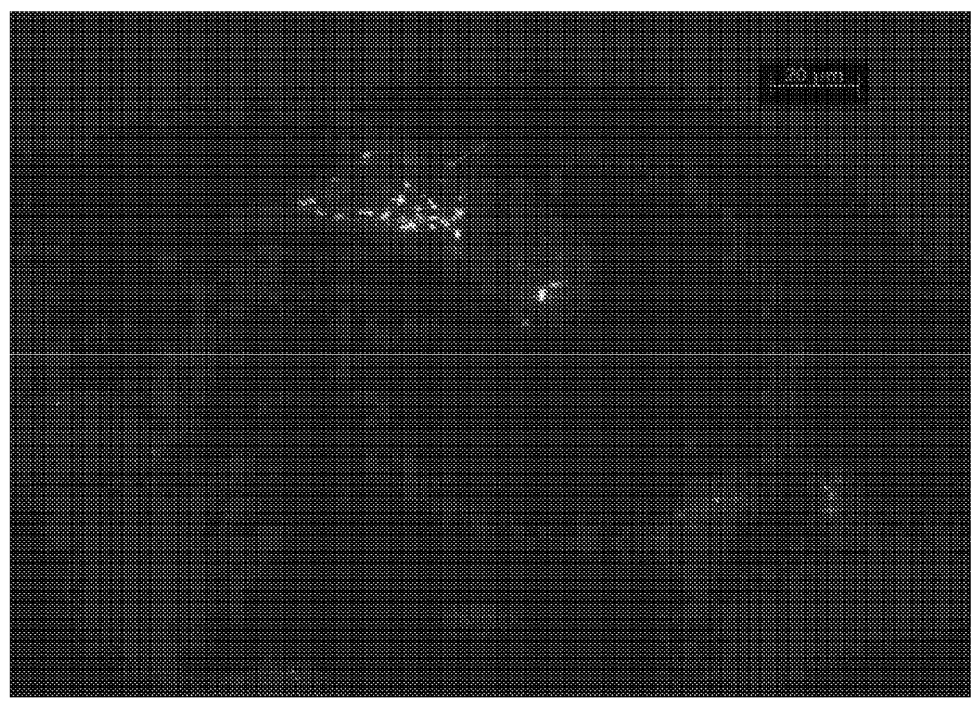
FIG. 4 shows, according to particular exemplary aspects, a Fluorescence microscopy of GFP expressing mutants in macrophages. Bovine monocyte derived macrophages were infected with GFP expressing mutants at MOI of 25 and visualized under fluorescence microscope with filters for FiTC and Tex Red. Bacteria are shown. A super-infected macrophage is visible. The ΔpknG mutant shown is representative of all GFP-expressing mutants in this study.

Applicants have demonstrated that GFP expressing mutants can be easily visualized within cultured macrophages under fluorescent microscope (FIG. 4). Importantly, the pWES4 plasmid (the plasmid for GFP in Map K10-GFP) introduced into *M. avium* and Map did not alter bacterial virulence (29). Therefore, it is evident that Map mutants containing GFP provide an advantage for investigating the function of deleted genes in host cells. In addition, GFP can be a potential antigenic marker for differentiation between wild-type and potential vaccine strains used as a live attenuated vaccine. By making GFP expressing mutants from the parent strain Map K10-GFP, Applicants provide a method to save at least several months required to introduce the GFP plasmid into mutant strains for this purpose. Moreover, Applicants have maximized the likelihood for mutants to express optimal GFP fluorescence as in the original Map K10-GFP host.

Figure 5:
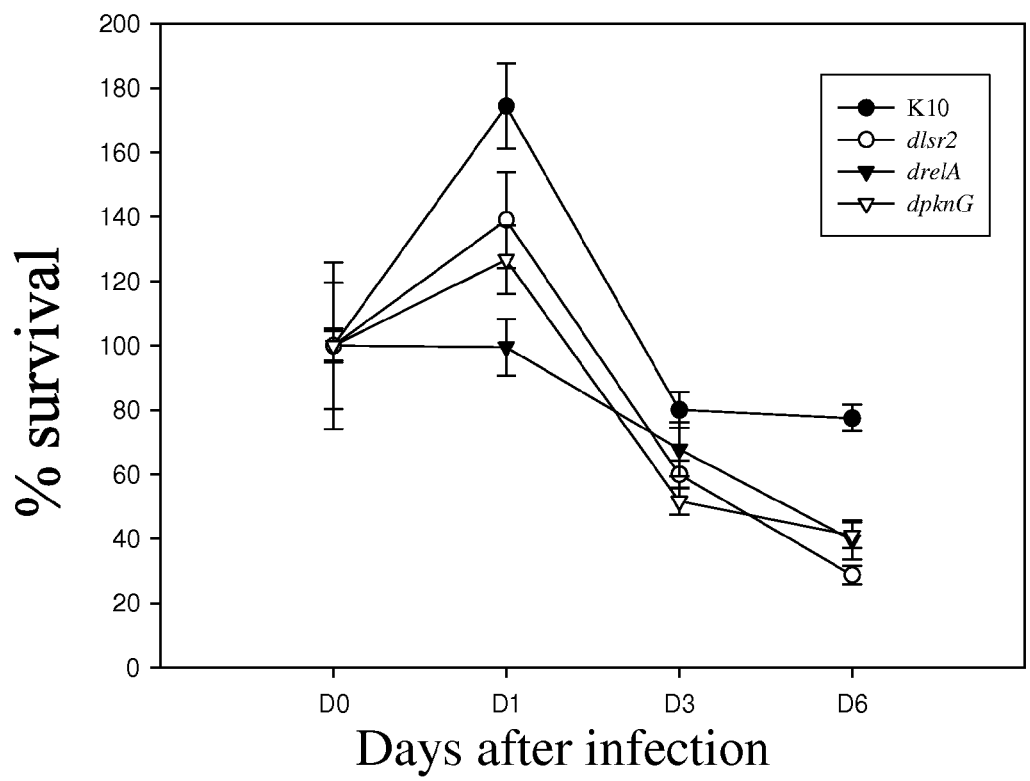
FIG. 5 shows, according to additional exemplary aspects, cultures of bovine macrophages that were infected at a multiplicity of infection (MOI) of 10 and examined over a 6 day period. Cultures were collected a 1, 3, and 6 days and lysed to free surviving bacteria. All 3 mutants exhibited a similar reduction in survival at 6 days. The findings indicate that disruption of these genes will impair Map capacity to survive in vitro and in vivo.

Example 6, herein below, shows that the disruption of the of pknG and relA and lsr2 genes in *M. avium* subsp. *paratuberculosis* (Map) will impair Map capacity to survive in vitro and in vivo. According to additional aspects, the inventive allelic exchange Map mutants have substantial utility for preparing vaccines, including, but not limited to live attenuated vaccine compositions. Specifically, cultures of bovine macrophages were infected at a multiplicity of infection (MOI) of 10 with pknG and relA and lsr2 gene mutants of *M. avium* subsp. *paratuberculosis* (Map), and examined over a 6-day period. Cultures were collected at 1, 3, and 6 days, and lysed to free surviving bacteria. FIG. 5 shows, according to additional exemplary aspects, that all 3 mutants exhibited a similar reduction in survival at 6 days. The findings indicate that disruption of these genes will impair Map capacity to survive in vitro and in vivo. According to additional aspects, such attenuated Map nonetheless maintain substantial immunogenicity, thus providing for a new class of Map vaccines, including but not limited to live attenuated vaccines.

Applicants have, therefore, established an efficient allelic exchange mutagenesis system for Map, and other slow-growing strains of mycobacteria, by generating various exemplary different targeted gene disruptions, one of which was disrupted by two different size deletions (relA), in Map K10 and Map K10-GFP. According to particular aspects, as in other mycobacterial species, these disrupted genes have important roles in virulence of Map. Along with the recently completed genome sequence (25) and a random transposon mutagenesis system for Map (12, 19, 32), Applicants' novel methods and compositions, will provide more insight into pathogenesis and will provide for development of effective vaccines for slow-growing strains of mycobacteria (e.g., Map, *M. bovis*, and *M. tuberculosis*).

EXAMPLE 1

Materials and Methods

Bacterial strains, vectors, and culture conditions. All strains of bacteria, plasmids, and phages used in this study are listed in TABLE 1. The *E. coli* Top10 strain was cultured in LB broth or LB agar (Difco, Md.) and used for cloning of homologous regions and construction of allelic exchange substrates (AESs) in pYUB854. The *E. coli* HB101 strain was used in an in vitro λ-packaging reaction (Gigapack III, Stratagene, Calif.). *M. smegmatis* mc$^2$155 was grown in basal Middlebrook 7H9 (Difco, Md.) broth medium containing 0.05% Tween 80 and prepared for generating phage lysates as previously described (9). Map strains were grown in Middlebrook 7H9 medium supplemented with 6.7% oleic acid-albumin-dextrose-catalase (OADC; Trek Diagnostic systems, OH), 2 µg/ml of mycobactin J (Allied Monitor, Mo.), and 0.05% Tween 80 (7H9 broth medium) or on Middlebrook 7H9 medium supplemented with 6.7% OADC, 6.7% egg yolk (Trek Diagnostic system, OH), 2 µg/ml of mycobactin J, and 1.5% agar base (Difco, Md.) (7H9 agar medium). Hygromycin (Hyg) was used at 50 µg/ml or 75 µg/ml for selection and subsequent culture of mutant colonies. Kanamycin (Kan) was used at 25 µg/ml for subculture of GFP-tagged mutants.

TABLE 1 plasmid, phage, and bacterial strains used in this study

| Phage, plasmid, or bacterial strain | Description | Source or reference |
|---|---|---|
| Bacterial strain | | |
| *E. coli* Top10 | A commercial strain used as a cloning host | Invitrogen |
| *E. coli* HB101 | E. coli strain without F factor | (9) |
| *M. smegmatis* | A high frequency transformation derivative of M. smegmatis mc$^2$ 6 mc$^2$ 155 | (33) |
| Map K10 | A virulent clinical isolate and sequencing project strain | (13, 17) |
| Map K10-GFP | Map K10 containing pWES4 for GFP expressing | (20) |
| Phage or plasmid | | |
| phAE87 | Conditionally replicating shuttle phasmid derivative of TM4 | (4) |
| pYUB 854 | Derivative of pYUB572. bla gene was replaced with hyg cassette | (5) |

Generation of specialized transducing mycobacteriophage containing AES. All primers used to generate upstream and downstream homologous regions and target genes are shown in TABLE 2. For the relA gene, two primer sets were designed to compare the efficiency of allelic exchange between a small (873-bp) and large (1737-bp) in-frame sequence deletion at the same genetic locus. The construction of each AES and subsequent delivery to the specialized transducing phage were done as previously reported (4, 9). Briefly, up- and downstream flanking fragments were amplified by PCR with primers designed to contain restriction sites corresponding to those present in the multiple cloning sites in cosmid pYUB854. Up- and downstream fragments were digested with appropriate enzymes (Table 2), and directionally cloned into pYUB854 on either side of the Hyg resistant gene to generate the AESs. The pYUB854 containing AESs were packaged into phasmid phAE87 using an in vitro λ-packaging solution (Gigapack III, Stratagene). The packaging solution was incubated with *E. coli* HB101 and plated on LB agar containing 150 µg/ml of Hyg. The phAE87 phasmid DNA containing the AESs was prepared from the pooled hygromycin-resistant (Hyg$^R$) colonies and electroporated into *M. smegmatis* mc$^2$ 155 to generate transducing mycobacteriophage. After incubating at the permissive temperature (30° C.) for 3 to 4 days, each plaque was tested for the temperature-sensitive phenotype. After confirming the correct construct of each AES by PCR with locus specific primers and restriction analysis, high titer transducing mycobacteriophage were prepared in MP buffer (50 mM Tris-HCl (pH 7.6), 150 mM NaCl, 10 mM MgCl$_2$, 2 mM CaCl$_2$), as previously described (9).

for pknG, relAS (S represents the small 873-bp sequence deletion at the relA locus, TABLE 2), and relAL (L represents large 1,737-bp sequence deletion at the relA locus, Table 2), as previously described for *M. tuberculosis* and *M. bovis* BCG (4) with slight modifications (termed Method A in this study). Briefly, Map was cultured in 10 ml of 7H9 broth medium with 1 ml of frozen stock in a 50-ml tube at 37° C. to an OD$_{600}$ of 0.6 (approximately 6×10$^8$ CFU/ml). The culture was centrifuged, resuspended, and incubated in 10 ml of 7H9 broth medium without Tween 80 at 37° C. for 24 h to remove any residual Tween 80 that can inhibit phage infection (9). Pelleted Map cells were resuspended in 2 ml of 7H9 broth medium without Tween 80. Each half of the suspension was incubated with 1 ml of MP buffer containing 10$^{10}$ PFU of each phage in a 2 ml screw cap tube at the non-permissive temperature (37° C.) for 4 h. The mixtures were added to 30 ml of 7H9 broth medium and cultured for an additional 24 h as a recovery time. The cultures were centrifuged, resuspended in 7H9 broth medium, and then plated on 7H9 agar

TABLE 2

Targeted Genes and Primers used for construction of allelic exchange substrates

| Targeted gene | Primer name[c] | Oligonecleotied sequence (expressed as 5' to 3' direction with 5' tagged restriction enzyme) | Expected deletion size | Gene bank access No. |
|---|---|---|---|---|
| pknG | pknGU-F (BglII) | TCGTGGTGTCGGTGGTCAACT SEQ ID NO: 8 | 1,737 bp | AE016958 |
|  | pknGU-R (HindIII) | GCCCTTGCTCTTCTTGGTGGA SEQ ID NO: 9 |  |  |
|  | pknGD-F (XbaI) | CACATCCTGGGCTTCCCGTTCA SEQ ID NO: 10 |  |  |
|  | pknGD-R (AflII) | TACCTGCGGCTGCTGCTCATCG SEQ ID NO: 11 |  |  |
| lsr2 | lsr2U-F (BglII) | TAGAAATGTACCCGTCGCTGTC SEQ ID NO: 12 | 311 bp | AE016958 |
|  | lsr2U-R (HindIII) | TTTGCCATTGGCTTACCCTC SEQ ID NO: 13 |  |  |
|  | lsr2D-F (XbaI) | CCTTCCACGCCGCAACCT SEQ ID NO: 14 |  |  |
|  | lsr2D-R (AflII) | GGCTCAGCTCCAGCACCTTC SEQ ID NO: 15 |  |  |
| relAS[a] | relASU-F (BglII) | CGACCGAATCGCTCAAGACG SEQ ID NO: 16 | 873 bp | AE016958 |
|  | relASU-R (HindIII) | GCGAACGACAGGTCCTCCAAC SEQ ID NO: 17 |  |  |
|  | relASD-F (XbaI) | GCAGTGGTTCGCCAAGGAG SEQ ID NO: 18 |  |  |
|  | relASD-R (AflII) | GGGTCGCCCATCTCAAAGG SEQ ID NO: 19 |  |  |
| relAL[b] | relALU-F (BglII) | AAGAAGATGTACGCGGTGAGC SEQ ID NO: 20 | 1,737 bp | AE016958 |
|  | relALU-R (HindIII) | CTTGAGCGATTCGGTCGG SEQ ID NO: 21 |  |  |
|  | relALD-F (XbaI) | ATCGACCAGACCGAGGAGGAC SEQ ID NO: 22 |  |  |
|  | relALD-R (AflII) | CCACAGACCAACGGCAAGG SEQ ID NO: 23 |  |  |

[a,b] S and L after gene name of relA represents relatively small size sequence deletion and large size sequence deletion at relA gene locus, respectively.
[c] Primer names were designated as the order of gene name, up- or downstream homologous region (U or D), forward or reverse primer (F or R) following hyphen.

Generation of targeted gene disruption in Map. Method A. The first transducing experiment in Map K10 or Map K10-GFP was performed with transducing phage containing AES medium containing 50 µg/ml Hyg. One to three hundred colonies were selected from each experiment after 8 wks of incubation for analysis.

Method B. Because of the appearance of numerous spontaneous Hyg$^R$ colonies in the initial platings of transduced bacteria, a new method of preparation of the transduced bacteria and culture was developed in a second trial (termed Method B). In this method, mycobacteriophage containing AES for relAS, or relAL were again transduced into Map K10 and Map K10-GFP. Bacteria were cultured in 50 ml 7H9 full broth medium to OD$_{600}$ of 0.6. After vigorous shaking, the cultures were allowed to stand for 10 min to allow large clumps of bacteria to sediment by gravity. Twenty-five ml of the top layer of each culture was then transferred into a 50 ml tube, and vigorously vortexed. The tubes were then allowed to stand for an additional 20 min without disturbance to allow further sedimentation of residual clumps. The top 10 ml of the cultures were then carefully collected for use. The rest of the procedures were essentially the same as described above for Method A with two exceptions. First, the amount of Hyg used in the selective agar was increased from 50 µg/ml to 75 µg/ml. Second, in the experiment for transducing the ΔrelAS construct in Map K10, bacteria were washed two times with MP buffer to remove residual Tween 80 (9), instead of incubating in 7H9 broth medium without Tween 80 as in all other experiments. As a control, Map receiving no phage were plated on the same selective agar. Subsequently, the third gene, lsr2, was mutagenized using Method B.

In addition, to evaluate whether the recovery time given in the above experiments has a critical effect for the efficiency of allelic exchange, Map receiving AES for relAL or lsr2 were directly plated onto the selective agar without the recovery time of 24 h. The results were compared to those in the experiment with a recovery time.

Isolation and confirmation of allelic exchange mutants. After 4 to 8 wk incubation on selective agar containing Hyg, each Hyg$^R$ colony was recultured on new selective agars containing Hyg alone or Hyg+Kan to expand bacterial cultures for subsequent analyses. After reculturing, the correct structure of the disrupted gene was confirmed for each colony by PCR. For ΔrelAS and Δlsr2, each PCR was performed with a specific primer set binding the flanking regions of the homologous section because the sizes of amplified fragments between wild and mutant types are clearly distinguished by PCR (over 1 Kb difference) (FIG. 1 and TABLE 1). The primer sets are as follows: for ΔrelAS, relL-3F (5'-TTCG-GAGGTGAGCATCGTGG-3'; SEQ ID NO:24) and relR-3R (5'-CCGACAACGGGTCCTGCTAC-3'; SEQ ID NO:25); for Δlsr2, lsrL-1F (5'-CCCCAATGTTGCAGACGC-3'; SEQ ID NO:26) and lsrR-1R (5'TCACCCGCTCGATTTCCTT-3'; SEQ ID NO:27). For ΔpknG and ΔrelAL, the correct construction of each side was confirmed separately with site specific primer sets because the sizes of PCR fragments are not well distinguished between mutant and wild type (178-bp difference) (FIG. 1 and TABLE 1). Each primer set was designed such that one primer bound within the hyg gene and one bound up- or downstream of the homologous region (FIG. 1). The primer sets are as follows: for the left side of ΔpknG, pknL-1F (5'-ACCAGAACTGCGACCTGACGG-3'; SEQ ID NO:28) and hyg-R (5'-GCCCTACCTGGTGAT-GAGCC-3'; SEQ ID NO:29); for the right side of ΔpknG, hyg-F (5'-CACGAAGATGTT GGTCCCGT-3'; SEQ ID NO:30) and pknR-1R (5'-TCCACCACAACACTCGTGCC-3'; SEQ ID NO:31); for the left side of ΔrelAL, relL-1F (5'-CAGGTGGACAACGCGATCG-3'; SEQ ID NO:32) and hyg-R (SEQ ID NO:29); for the right side of ΔrelAL, hyg-F (SEQ ID NO:30) and relR2R (5'-TGCGTCGTTGAT-GAGGGTT-3'; SEQ ID NO:33). For further confirmation, sequencing analysis was performed on one or two isolates from each mutant group in Map K10 and Map K10-GFP.

Transduction frequencies were calculated as (X-Y)/Z, where X was the number of Hyg$^R$ colonies obtained, Y was the number of spontaneous Hyg$^R$ colonies from control cells which received no phage, and Z was the number of input cells for each experiment. Allelic exchange frequency was calculated as the percentage of allelic exchange in the population of Hyg$^R$ colonies (4).

Expression analysis of disrupted Map genes. RNA expression of the disrupted gene was also checked by RT-PCR. Total RNA of Map K10 and two isolates from each mutant group in Map K10 and Map K10-GFP in stationary phase was isolated using the FastRNA Pro Blue Kit (Q-Biogene, Ohio) and treated two times with DNase I (Invitrogen, Calif.). cDNAs were synthesized with SuperScript III Reverse Transcriptase (Invitrogen, Calif.) and used as PCR templates with a specific primer set for each targeted gene.

Visualization of GFP expressing mutants in bovine monocyte-derived macrophages using fluorescence microscopy. Bovine peripheral blood was collected via jugular venipuncture into vacutainer bottles. Monocyte-derived macrophages were prepared as previously reported (35), and infected with mutant strains expressing GFP at a multiplicity of infection (MOI) of 25. After 2 h incubation, the medium was removed and the plate washed 3 times with phosphate buffered saline (PBS; pH 7.4). Macrophages were detached from plates with PBS containing 10 mM EDTA, centrifuged, and resuspended in a small amount of PBS. One drop of cell-suspension was mounted on a slide, and covered with a coverslip. Without macrophage fixation, the slide was immediately examined with a fluorescence microscope (Axioscope2 FS plus, Zeiss) using filters for FiTC and Tex Red.

EXAMPLE 2

Disruption of PknG and RelA in *M. Avium* Subsp. *Paratuberculosis*

Overview:

Disruption of pknG and relA in *M. avium* subsp. *paratuberculosis*. Allelic exchange mutagenesis using specialized transduction has been used successfully in some slow growing mycobacteria, including *M. tuberculosis, M. bovis* and *M. avium* (4, 27). However, successful use of the technology has not been previously reported in Map. Applicants have improved and extended this approach to develop, or the first time, efficient targeted gene disruptions in Map, one of the slowest growing mycobacterial species with a generation time (24 h or longer) that is at least 1½ times longer than that of *M. tuberculosis* (31).

Methods:

See Example 1 above.

Results:

Using Method A, which was based on a protocol developed for *M. tuberculosis* and *M. bovis* BCG (4), Map K10 and Map K10-GFP were infected with a specialized transducing phage carrying AES for pknG or relAS. More than a thousand colonies were visible after 8 wk of incubation in each of the cultures of Map and Map-GFP transduced with the pknG or relAS AES. However, screening of 300 colonies from each experiment by PCR revealed that there was a high level of spontaneous $Hyg^R$. Moreover, this initial trial only yielded 7 ΔpknG mutants each in Map K10 and Map K10-GFP. No mutants were detected in the screening of cultures of Map K10 and Map K10-GFP transduced with the relAS AES (TABLE 3). Furthermore, no mutants were detected in two additional experiments with the relAS AES (data not shown). Based on these results, we hypothesized that the sizes of inserted and deleted sequences at the recombination locus might be interfering with the efficiency of allelic exchange. The size of inserted sequence was similar to that of the deleted sequence in ΔpknG (1,915-bp vs. 1,737-bp) but larger than that of deleted sequence in ΔrelAS (1,915-bp vs. 873-bp). Therefore, another transducing phage carrying an AES for the relA deletion (relAL) was designed to delete 1,737-bp in the relA locus and tested with the same method. However, no mutants were detected in the screening of 150 colonies each of Map K10 and Map K10 GFP transduced with the relAL AES (TABLE 3).

Although some mutants were generated in the ΔpknG experiments, the frequency of allelic exchange in comparison to those for *M. tuberculosis* and *M. bovis* (4) was very low (0-2.3% vs. 90-100%). These findings underscored the difficulties encountered when working with Map and suggested the methodology would have to substantially improved to enable efficient use this system of transduction as a routine laboratory procedure.

Hyg$^R$, cultures were subjected to gravity sedimentation to remove most bacterial clumps. To minimize the frequency of spontaneous mutants, we also increased the concentration of Hyg from 50 to 75 μg/ml in the second trial and departed from the drug concentration typically used for other mycobacteria (21, 27).

Figure 2:
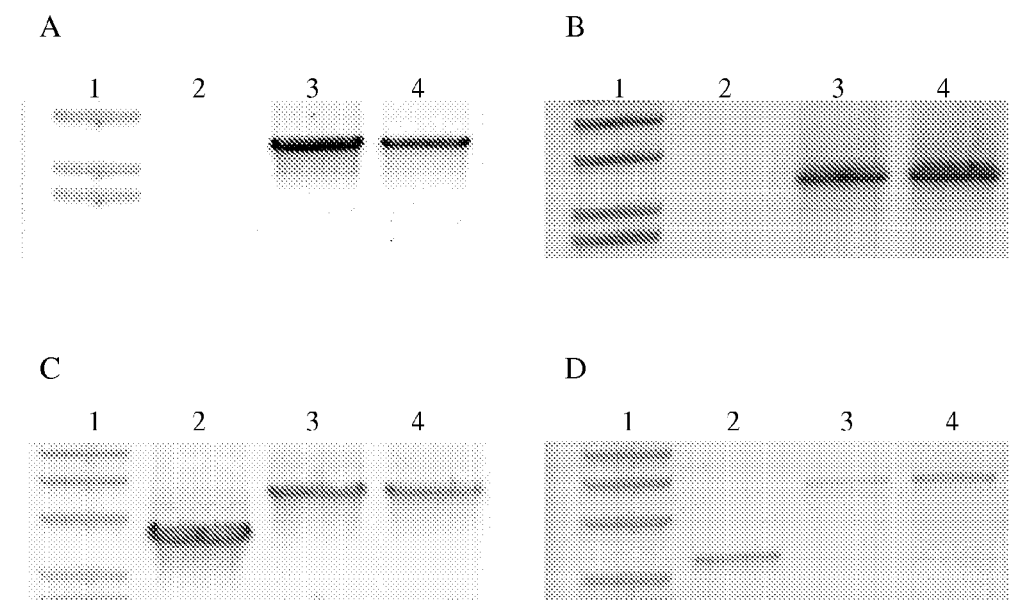
FIG. 2 shows, according to particular exemplary aspects, a PCR identification for specific gene construction in mutants. (A) PCR for ΔpknG. (B) PCR for ΔrelAL. (C) PCR for ΔrelAS. (D) PCR for Δlsr2. Lane assignments for all panels are: lane 1, DNA size marker; lane 2, wild type (Map K10); lane 3, mutant in Map K10; lane 4, mutant in Map K10-GFP. The primer sites for ΔpknG (A) and ΔrelAL (B) PCR reactions were located on Hyg gene (inserted gene) for forward primer and out side of downstream homologous region of each disrupted gene for reverse primer. Note that the wild type does not amplify in those two panels because of the primer design. The primer sites for ΔrelAS (C) and Δlsr2 (D) PCR reactions were located outside of up- and downstream homologous regions of each disrupted gene, enabling the identification of mutants based on size of the amplified fragments.
Figure 3:
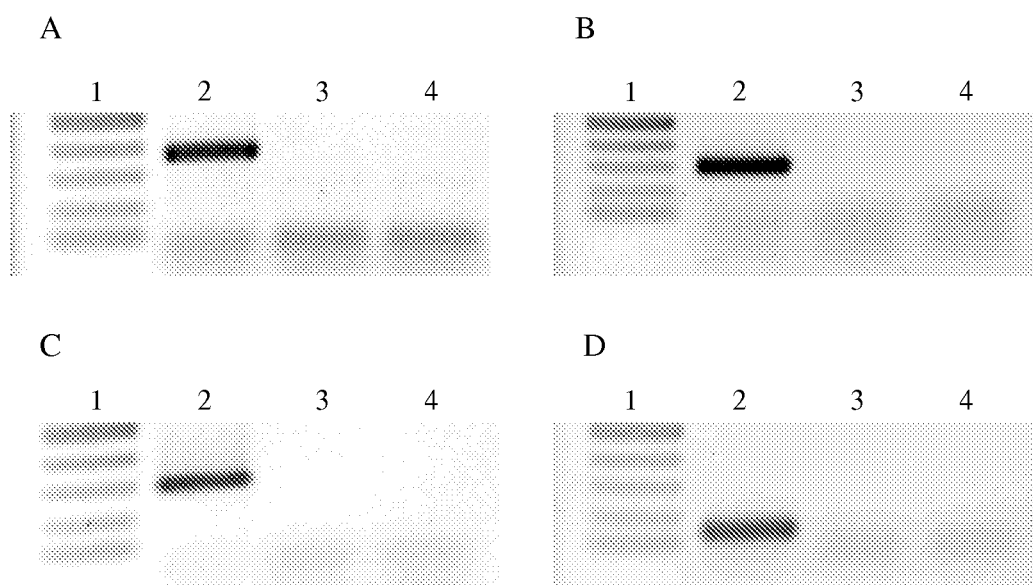
FIG. 3 shows, according to particular exemplary aspects, a RT-PCR analysis of gene expression in Map strains. Amplification of cDNA for pknG (A; 380-bp), for relA from ΔrelAL (B; 303-bp) and ΔrelAS mutants (C; 303-bp), and for lsr2 (D; 145-bp). Lane assignments for all panels are: lane 1, DNA marker; lane 2, wild type (Map K10); lane 3, mutant in Map K10; lane 4, mutant in Map K10-GFP.

After 4 to 8 wk incubation, 35 to 500 Hyg$^R$ colonies were generated in the experiment of relA deletion using Method B. Colonies from each type of targeted gene deletion were transferred onto new agar plates containing Hyg. The mutant colonies for ΔpknG and ΔrelA were identified by PCR using locus specific primers (FIG. 2). Furthermore, the correct position of allelic exchange was confirmed by sequencing analysis in one or two mutant isolates from each mutant group in Map K10 and Map K10-GFP (data not shown). In addition, lack of RNA expression of deleted genes was also confirmed by RT-PCR in 2 isolates from each mutant group in Map K10 and Map K10-GFP (FIG. 3). Both target genes were expressed in the control strain (Map K10), but they were absent in respective gene deleted mutants. In comparison with the first trial with Method A, the allelic exchange frequencies in the second trial with Method B were greatly increased (from 0-2.3% to

TABLE 3

Efficiency of allelic exchange in Map

| Host strain | Genotype | Method[c] | No. of allelic exchange/ no. of tested Hyg$^R$ (%)[e] | No. of total Hyg$^R$ | Transduction frequency |
|---|---|---|---|---|---|
| Map K10 | ΔpknG | A | 7/300 (2.3) | N/A[f] | N/A |
| | ΔrelAS[a] | A | 0/300 (0.0) | N/A | N/A |
| | ΔrelAL[b] | A | 0/150 (0.0) | N/A | N/A |
| | ΔrelAS[a] | B[d] | 2/35 (5.7) | 35 | $9.3 \times 10^{-9}$ |
| | ΔrelAL[b] | B | 48/50 (96.0) | 291 | $9.5 \times 10^{-8}$ |
| | Δlsr2 | B | 50/50 (100.0) | 738 | $2.4 \times 10^{-7}$ |
| Map K10-GFP | ΔpknG | A | 7/300 (2.3) | N/A | N/A |
| | ΔrelAS[a] | A | 0/300 (0.0) | N/A | N/A |
| | ΔrelAL[b] | A | 0/150 (0.0) | N/A | N/A |
| | ΔrelAS[a] | B | 33/35 (94.3) | 499 | $1.6 \times 10^{-7}$ |
| | ΔrelAL[b] | B | 39/50 (78.0) | 448 | $1.5 \times 10^{-7}$ |
| | Δlsr2 | B | 50/50 (100.0) | 438 | $1.4 \times 10^{-7}$ |

[a,b]S and L after relA represents small sequence deletion and large sequence deletion at relA gene locus, respectively.
[c]Method A was used in the first trial, and Method B in the second trial. For the detailed information, see the text in materials and methods.
[d]The difference from other experiments with Method B was that Map was washed with MP buffer to remove residual Tween 80 before absorbing phage. For the detailed information, see the text in materials and methods part.
[e]The percentage in the parenthesis is the allelic exchange frequency.
[f]N/A, not-available

EXAMPLE 3

Demonstration of Efficient Allelic Exchange Mutagenesis in Map by Specialized Transduction; and Demonstration of Disruption of the lsr2 Gene Overview:

Efficiency of allelic exchange mutagenesis in Map by specialized transduction. After observing a high rate of spontaneous Hyg$^R$ in the first trial with Method A, the procedure was modified to determine if the efficiency of allelic exchange could be increased. We focused on reducing the unanticipated generation of a high frequency of spontaneous Hyg$^R$ colonies.

Methods:

See Examples 1-2 above.

Results:

Method B. Applicants hypothesized that the high level of spontaneous Hyg$^R$ colonies was in part due to excessive clumping of Map in the broth culture as compared with similar cultures of *M. bovis* (data not shown). Since vigorous vortexing and pipeting did not reduce the rate of spontaneous 78-96%; TABLE 3). Compared to incubation in 7H9 broth medium without Tween 80, washing with MP buffer to remove the residual Tween 80 showed a decrease in the allelic exchange frequency and transduction frequency (TABLE 3). Contrary to our hypothesis, the size of the deletion in relA did not have a significant effect on the frequency of mutants generated with Method B (873-bp deletion vs. 1,915-bp insertion and 1,737-bp deletion vs. 1,915-bp insertion; TABLES 2 and 3).

To test whether the optimized method (Method B) works well in additional gene deletions, a third gene, lsr2, was selected for disruption. Lsr2 is a cytosolic protein implicated in cell wall lipid synthesis, which has an important role in colony morphology and biofilm formation in *M. smegmatis* (14). The confirmation method for Lsr2 deletion was exactly the same as above (FIGS. 2 and 3). As shown in TABLE 3, the generation of Δlsr2 with Method B showed a 100% correlation of Hyg$^R$ to successful allelic exchange. These data indicate method B works equally well with other genes.

The effect of recovery time between 0 and 24 h was compared in three knockout experiments. For the ΔrelAL mutation in Map K10-GFP and the Δlsr2 mutation in Map K10, the total numbers of Hyg$^R$ colonies were increased about 2 times after 24 h incubation in 7H9 broth medium before plating, which is consistent with one replication cycle of Map, 24-48 h. However, for the ΔrelAL mutation in Map K10, the number of Hyg$^R$ decreased after 24 h incubation.

Contrary to previous findings with *M. bovis* BCG (4), which showed the highest allelic exchange frequency with 24 h of recovery time, the allelic exchange frequency in each experiment was virtually the same with and without the recovery time in the present study (TABLE 4).

EXAMPLE 4

Efficient Allelic Exchange Mutagenesis in Other Exemplary Map loci

Efficient allelic exchange mutagenesis in other exemplary Map loci. The complete genomic sequence of *Mycobacterium avium* subsp. *paratuberculosis* K-10, is currently known (see accession number AE016958; gi:41400296), and 4,350 protein encoding loci have been currently identified.

TABLE 4

Effect of recovery time on the efficiency of allelic exchange mutagenesis

| | ΔrelAL K10 | | ΔrelAL K10-GFP | | Δlsr2 K10 | |
|---|---|---|---|---|---|---|
| Recovery time (h) | ΔrelAL/Hyg$^R$ (%)$^a$ | No. of total Hyg$^R$ | ΔrelAL/Hyg$^R$ (%)$^a$ | No. of total Hyg$^R$ | Δlsr2/Hyg$^R$ (%)$^a$ | No. of total Hyg$^R$ |
| 0 | 50/50 (100) | 656 | 39/50 (78) | 266 | 50/50 (100) | 402 |
| 24 | 48/50 (96) | 291 | 42/50 (84) | 448 | 50/50 (100) | 738 |

$^a$The percentage in parenthesis indicates the allelic exchange frequency.

In preferred aspects Method B is practiced as follows: The mycobacteria are cultured (broth cultured) followed by gravity sedimentation, low-speed centrifugation (e.g., 3,700×g), resuspension in medium without tween 80 and incubation to remove residual tween 80, low-speed centrifugation (e.g., 3,700×g), resuspension in a small volume of MP buffer (e.g., 1 ml), followed by mixing with same volume of MP buffer containing mycobacteriophage packaged with AES and incubating for transduction (optionally including an outgrowth incubation period in full medium), low-speed centrifugation (e.g., 3,700×g), and resuspension in a small volume of full medium, followed by plating.

Preferably, the centrifugation steps are all low-speed centrifugation (e.g., 3,700×g). Although in the present studies adding an outgrowth period did not enhance efficiency, this step did not decrease the efficiency and increased the total colony count. Therefore, Applicants regard this step as optional.

Applicants' invention provides, for the first time, an efficient system for generating allelic exchange mutants in *Mycobacterium avium* subsp. *paratuberculosis* (Map). According to additional aspects, the presently disclosed methods can be used to target any of the 4350 known protein encoding loci in Map.

TABLE 5 below, for example, lists (in addition to PknG, RelA and Lsr2, discussed above) other preferred, exemplary genes for which allelic exchange mutants can be generated using the disclosed inventive methods. Such targets include, but are not limited to, pknG, relA, lsr2, panC, panD, proC, trpD, sapM (MAP3432), lysA_1, leuD, leuC, etc. In further aspects, the *M. avium* homolog of the pcaA gene, recognized in the art as being important for *M. tuberculosis* pathogenesis, is targeted by the inventive methods. Yet further aspects comprise deletions of regions controlling vitamin (e.g., pantothenic acid, or nicotinamide adenine dinucleotide (NAD)), or amino acid (e.g., praline, tryptophane, leucine or lysine) production.

TABLE 5

*Mycobacterium avium* subsp. *paratuberculosis* K-10, complete genome
(AE016958; gi: 41400296)

| Product Name | Start (nucleotide position) | End | Strand | Length (amino Acids) | Gi | GeneID | Locus | Locus_tag |
|---|---|---|---|---|---|---|---|---|
| PknG<br>SEQ ID NO: 1 (DNA)<br>SEQ ID NO: 2 (protein) | 4356884 | 4359175 | − | 763 | 41409991 | 2718490 | pknG | MAP3893c |
| RelA<br>SEQ ID NO: 4 (DNA)<br>SEQ ID NO: 5 (protein) | 1095830 | 1098196 | + | 788 | 41407145 | 2717869 | relA | MAP1047 |
| Lsr2<br>SEQ ID NO: 6 (DNA)<br>SEQ ID NO: 7 (protein) | 487623 | 487961 | + | 112 | 41406558 | 2720570 | lsr2 | MAP0460 |
| pantoate--beta-alanine ligase<br>SEQ ID NO: 34 (DNA)<br>SEQ ID NO: 35 (protein) | 483757 | 484683 | + | 308 | 41406554 | 2717541 | panC | MAP0456 |
| aspartate alpha-decarboxylase<br>SEQ ID NO: 36 (DNA)<br>SEQ ID NO: 37 (protein) | 484683 | 485114 | + | 143 | 41406555 | 2720293 | panD | MAP0457 |
| pyrroline-5-carboxylate reductase | 4448783 | 4449679 | + | 298 | 41410089 | 2721460 | proC | MAP3991 |

TABLE 5-continued

Mycobacterium avium subsp. paratuberculosis K-10, complete genome
(AE016958; gi: 41400296)

| Product Name | Start (nucleotide position) | End | Strand | Length (amino Acids) | Gi | GeneID | Locus | Locus_tag |
|---|---|---|---|---|---|---|---|---|
| SEQ ID NO: 38 (DNA) SEQ ID NO: 39 (protein) anthranilate phosphoribosyltransferase SEQ ID NO: 40 (DNA) SEQ ID NO: 41 (protein) | 2132528 | 2133631 | − | 367 | 41408029 | 2720375 | trpD | MAP1931c |
| hypothetical protein MAP3432 SEQ ID NO: 42 (DNA) SEQ ID NO: 43 (protein) | 3811490 | 3812392 | + | 300 | 41409530 | 2719192 | (sapM) | MAP3432 |
| LysA_1 SEQ ID NO: 44 (DNA) SEQ ID NO: 45 (protein) | 1023968 | 1025302 | − | 444 | 41407084 | 2719301 | lysA_1 | MAP0986c |
| isopropylmalate isomerase small subunit SEQ ID NO: 46 (DNA) SEQ ID NO: 47 (protein) | 3365224 | 3365826 | − | 200 | 41409123 | 2717943 | leuD | MAP3025c |
| isopropylmalate isomerase large subunit SEQ ID NO: 48 (DNA) SEQ ID NO: 49 (protein) | 3365846 | 3367276 | − | 476 | 41409124 | 2717949 | leuC | MAP3026c |

EXAMPLE 5

Generation of GFP Tagged Mutants in Map

Overview:

Generation of GFP tagged mutants in Map. Expression of GFP in the M. avium subsp. avium is variable with only few transformants expressing high GFP levels (29). Thus, to construct GFP-tagged mutants with equivalent high fluorescence levels, it may be useful to carry out the allelic exchange directly in a Map host with optimal GFP expression, such as Applicants' Map K10-GFP.

Methods:

See Example 1 above.

Results:

Applicants' data shows that allelic exchange mutagenesis occurred in Map K10-GFP at the same rate as in Map K10 (TABLES 3 and 4). Every ten isolates of each mutant made from Map K10-GFP, except ΔpknG (7 isolates), were examined by fluorescence microscopy for the presence of GFP (TABLE 6). Even after extensive incubation without antibiotic pressure for the GFP plasmid (Kan), some mutant strains still expressed GFP. In contrast, the ratio of GFP expression in ΔrelAL was half of ΔrelAS, which suggests a longer time of incubation in absence of antibiotic pressure may either increase the loss of the plasmid or decrease it to undetectable levels of GFP fluorescence due to undesirable mutational effects.

TABLE 6

Stability of GFP plasmid in Map during allelic exchange mutagenesis

| Mutant | Incubation time without Kan (wk)[a] | No. of GFP expressing mutants/ No. of examined mutants |
|---|---|---|
| ΔpknG K10-GFP | 8 | 6/7 |
| ΔrelAS K10-GFP | 8 | 10/10 |
| ΔrelAL K10-GFP | 12 | 5/10 |
| Δlsr2 K10-GFP | 8 | 2/10 |

[a]Kan is the selective antibiotic for GFP expressing plasmid (pWES4).

Applicants also examined the GFP tagged mutants as a useful tool for tracing the mutant within bovine macrophages after infection. The presence of GFP expressing mutants was clearly detected by fluorescence microscopy (FIG. 4).

EXAMPLE 6

Disruption of the of PknG and RelA and Lsr2 Genes in M. Avium Subsp. Paratuberculosis (Map) Will Impair Map Capacity to Survive in vitro and in vivo Overview:

Disruption of the of pknG and relA and lsr2 genes in M. avium subsp. paratuberculosis (Map) will impair Map capacity to survive in vitro and in vivo. According to additional aspects, the inventive allelic exchange Map mutants have substantial utility for preparing vaccines, including, but not limited to attenuated vaccine compositions.

Methods:

Cultures of bovine macrophages were infected at a multiplicity of infection (MOI) of 10 with pknG and relA and lsr2 gene mutants of M. avium subsp. paratuberculosis (Map), and examined over a 6-day period. Cultures were collected at 1, 3, and 6 days, and lysed to free surviving bacteria.

Results:

FIG. 5 shows, according to additional exemplary aspects, that all 3 mutants exhibited a similar reduction in survival at 6 days. The findings indicate that disruption of these genes will impair Map capacity to survive in vitro and in vivo. According to additional aspects, such attenuated Map nonetheless maintains substantial immunogenicity, thus providing for a new class of Map vaccines, including but not limited to live attenuated vaccines.

CITED REFERENCES

1. Aldovini, A., R. N. Husson, and R. A. Young. 1993. The uraA locus and homologous recombination in Mycobacterium bovis BCG. J Bacteriol 175:7282-9.

2. Azad, A. K., T. D. Sirakova, L. M. Rogers, and P. E. Kolattukudy. 1996. Targeted replacement of the mycocerosic acid synthase gene in *Mycobacterium bovis* BCG produces a mutant that lacks mycosides. Proc Natl Acad Sci USA 93:4787-92.
3. Balasubramanian, V., M. S. Pavelka, Jr., S. S. Bardarov, J. Martin, T. R. Weisbrod, R. A. McAdam, B. R. Bloom, and W. R. Jacobs, Jr. 1996. Allelic exchange in *Mycobacterium tuberculosis* with long linear recombination substrates. J Bacteriol 178:273-9.
4. Bardarov, S., S. Bardarov Jr, Jr., M. S. Pavelka Jr, Jr., V. Sambandamurthy, M. Larsen, J. Tufariello, J. Chan, G. Hatfull, and W. R. Jacobs Jr, Jr. 2002. Specialized transduction: an efficient method for generating marked and unmarked targeted gene disruptions in *Mycobacterium tuberculosis, M. bovis* BCG and *M. smegmatis*. Microbiology 148:3007-17.
5. Bardarov, S., J. Kriakov, C. Carriere, S. Yu, C. Vaamonde, R. A. McAdam, B. R. Bloom, G. F. Hatfull, and W. R. Jacobs, Jr. 1997. Conditionally replicating mycobacteriophages: a system for transposon delivery to *Mycobacterium tuberculosis*. Proc Natl Acad Sci USA 94:10961-6.
6. Benedictus, G., A. A. Dijkhuizen, and J. Stelwagen. 1987. Economic losses due to *paratuberculosis* in dairy cattle. Vet Rec 121:142-6.
7. Berthet, F. X., M. Lagranderie, P. Gounon, C. Laurent-Winter, D. Ensergueix, P. Chavarot, F. Thouron, E. Maranghi, V. Pelicic, D. Portnoi, G. Marchal, and B. Gicquel. 1998. Attenuation of virulence by disruption of the *Mycobacterium tuberculosis* erp gene. Science 282:759-62.
8. Boshoff, H. I., and V. Mizrahi. 2000. Expression of *Mycobacterium smegmatis* pyrazinamidase in *Mycobacterium tuberculosis* confers hypersensitivity to pyrazinamide and related amides. J Bacteriol 182:5479-85.
9. Braunstein, M., S. S. Bardarov, and W. R. Jacobs, Jr. 2002. Genetic methods for deciphering virulence determinants of *Mycobacterium tuberculosis*. Methods Enzymol 358:67-99.
10. Braunstein, M., A. M. Brown, S. Kurtz, and W. R. Jacobs, Jr. 2001. Two nonredundant SecA homologues function in mycobacteria. J Bacteriol 183:6979-90.
11. Camacho, L. R., D. Ensergueix, E. Perez, B. Gicquel, and C. Guilhot. 1999. Identification of a virulence gene cluster of *Mycobacterium tuberculosis* by signature-tagged transposon mutagenesis. Mol Microbiol 34:257-67.
12. Cavaignac, S. M., S. J. White, G. W. de Lisle, and D. M. Collins 2000. Construction and screening of *Mycobacterium paratuberculosis* insertional mutant libraries. Arch Microbiol 173:229-31.
13. Chacon, O., L. E. Bermudez, and R. G. Barletta. 2004. Johne's disease, inflammatory bowel disease, and *Mycobacterium paratuberculosis*. Annu Rev Microbiol 58:329-63.
14. Chen, J. M., G. J. German, D. C. Alexander, H. Ren, T. Tan, and J. Liu. 2006. Roles of Lsr2 in colony morphology and biofilm formation of *Mycobacterium smegmatis*. J Bacteriol 188:633-41.
15. Cox, J. S., B. Chen, M. McNeil, and W. R. Jacobs, Jr. 1999. Complex lipid determines tissue-specific replication of *Mycobacterium tuberculosis* in mice. Nature 402:79-83.
16. Dahl, J. L., C. N. Kraus, H. I. Boshoff, B. Doan, K. Foley, D. Avarbock, G. Kaplan, V. Mizrahi, H. Rubin, and C. E. Barry, 3rd. 2003. The role of RelMtb-mediated adaptation to stationary phase in long-term persistence of *Mycobacterium tuberculosis* in mice. Proc Natl Acad Sci USA 100:10026-31.
17. Foley-Thomas, E. M., D. L. Whipple, L. E. Bermudez, and R. G. Barletta. 1995. Phage infection, transfection and transformation of *Mycobacterium avium* complex and *Mycobacterium paratuberculosis*. Microbiology 141 (Pt 5):1173-81.
18. Harris, N. B., and R. G. Barletta. 2001. *Mycobacterium avium* subsp. *paratuberculosis* in Veterinary Medicine. Clin Microbiol Rev 14:489-512.
19. Harris, N. B., Z. Feng, X. Liu, S. L. Cirillo, J. D. Cirillo, and R. G. Barletta. 1999. Development of a transposon mutagenesis system for *Mycobacterium avium* subsp. *paratuberculosis*. FEMS Microbiol Lett 175:21-6.
20. Harris, N. B., D. K. Zinniel, M. K. Hsieh, J. D. Cirillo, and R. G. Barletta. 2002. Cell sorting of formalin-treated pathogenic *Mycobacterium paratuberculosis* expressing GFP. Biotechniques 32:522-4, 526-7.
21. Hatfull, G. F., and W. R. Jacobs. 2000. Molecular genetics of mycobacteria. ASM Press, Washington, D.C.
22. Johnson-Ifearulundu, Y. J., J. B. Kaneene, D. J. Sprecher, J. C. Gardiner, and J. W. Lloyd. 2000. The effect of subclinical *Mycobacterium paratuberculosis* infection on days open in Michigan, USA, dairy cows. Prev Vet Med 46:171-81.
23. Kalpana, G. V., B. R. Bloom, and W. R. Jacobs, Jr. 1991. Insertional mutagenesis and illegitimate recombination in mycobacteria. Proc Natl Acad Sci USA 88:5433-7.
24. Knipfer, N., A. Seth, and T. E. Shrader. 1997. Unmarked gene integration into the chromosome of *Mycobacterium smegmatis* via precise replacement of the pyrF gene. Plasmid 37:129-40.
25. Li, L., J. P. Bannantine, Q. Zhang, A. Amonsin, B. J. May, D. Alt, N. Banerji, S. Kanjilal, and V. Kapur. 2005. The complete genome sequence of *Mycobacterium avium* subspecies *paratuberculosis*. Proc Natl Acad Sci USA 102:12344-9.
26. McFadden, J. 1996. Recombination in mycobacteria. Mol Microbiol 21:205-11.
27. Otero, J., W. R. Jacobs, Jr., and M. S. Glickman. 2003. Efficient allelic exchange and transposon mutagenesis in *Mycobacterium avium* by specialized transduction. Appl Environ Microbiol 69:5039-44.
28. Ott, S. L., S. J. Wells, and B. A. Wagner. 1999. Herd-level economic losses associated with Johne's disease on US dairy operations. Prev Vet Med 40:179-92.
29. Parker, A. E., and L. E. Bermudez. 1997. Expression of the green fluorescent protein (GFP) in *Mycobacterium avium* as a tool to study the interaction between *Mycobacteria* and host cells. Microbial Pathogenesis 22:193-198.
30. Pavelka, M. S., Jr., and W. R. Jacobs, Jr. 1999. Comparison of the construction of unmarked deletion mutations in *Mycobacterium smegmatis, Mycobacterium bovis bacillus* Calmette-Guerin, and *Mycobacterium tuberculosis* H37Rv by allelic exchange. Bacteriol 181:4780-9.
31. Shin, S. J., J. H. Han, E. J. Manning, and M. T. Collins 2007. Rapid and reliable method for quantification of *Mycobacterium paratuberculosis* using the BACTEC MGIT 960 system. J Clin Microbiol.
32. Shin, S. J., C. W. Wu, H. Steinberg, and A. M. Talaat. 2006. Identification of novel virulence determinants in *Mycobacterium paratuberculosis* by screening a library of insertional mutants. Infect Immun 74:3825-33.
33. Snapper, S. B., R. E. Melton, S. Mustafa, T. Kieser, and W. R. Jacobs, Jr. 1990. Isolation and characterization of efficient plasmid transformation mutants of *Mycobacterium smegmatis*. Mol Microbiol 4:1911-9.
34. Walburger, A., A. Koul, G. Ferrari, L. Nguyen, C. Prescianotto-Baschong, K. Huygen, B. Klebl, C. Thompson, G.

Bacher, and J. Pieters. 2004. Protein kinase G from pathogenic mycobacteria promotes survival within macrophages. Science 304:1800-4.

35. Weiss, D. J., O. A. Evanson, A. Moritz, M. Q. Deng, and M. S. Abrahamsen. 2002. Differential responses of bovine macrophages to *Mycobacterium avium* subsp. *paratuberculosis* and *Mycobacterium avium* subsp. *avium*. Infect Immun 70:5556-61.

36. B. A. Rideout, S. T. Brown, W. C. Davis, J. M. Gay, R. A. Giannella, M. E. Hines, W. D. Hueston, and L. J. Hutchinson. *Diagnosis and control of Johne's disease*, Washington, D.C.; The National Academy Press, 2003. 229 pages 37. Sambandamurthy, V. K., X. Wang, B. Chen, R. G. Russell, S. Derrick, F. M. Collins, S. L. Morris, and W. R. Jacobs, Jr. 2002. A pantothenate auxotroph of *Mycobacterium tuberculosis* is highly attenuated and protects mice against tuberculosis. Nat Med 8:1171-4.

38. Smith, D. A., T. Parish, N. G. Stoker, and G. J. Bancroft. 2001. Characterization of auxotrophic mutants of *Mycobacterium tuberculosis* and their potential as vaccine candidates. Infect Immun 69:1142-50.

39. Vergne, I., J. Chua, H. H. Lee, M. Lucas, J. Belisle, and V. Deretic. 2005. Mechanism of phagolysosome biogenesis block by viable *Mycobacterium tuberculosis*. Proc Natl Acad Sci USA 102:4033-8.

The invention claimed is:

1. A method for directed allelic exchange mutagenesis of slow-growing *mycobacterium* (sp), comprising:

providing a conditionally replicating transducing mycobacteriophage containing an allelic exchange substrate (AES), the AES comprising a selectable gene flanked by upstream and downstream homologous regions that flank a target locus or gene;

culturing a slow-growing mycobacterial strain characterized by clumping during culturing, followed by gravity sedimentation to provide a supernatant fraction and a sediment fraction, low-speed centrifugation of the supernatant fraction to provide a first low-speed mycobacterial pellet, and re-suspension of the low-speed mycobacterial pellet in culture medium suitable for transducing;

culturing the re-suspended slow-growing mycobacterial strain in the presence of the transducing mycobacteriophage at a non-permissive temperature to provide a mycobacteriophage-contacted culture;

withdrawing an amount of the mycobacteriophage-contacted culture; and selecting, using the withdrawn amount and a suitable selection medium, allelic exchange mutants of the slow-growing mycobacterial strain.

2. The method of claim 1, wherein the slow-growing strain of mycobacteria is *Mycobacterium avium* subsp. *paratuberculosis* (Map), Map K10, *Mycobacterium bovis*, or *Mycobacterium tuberculosis*.

3. The method of claim 1, wherein the selectable gene is hygromycin resistant ($Hyg^R$).

4. The method of claim 1, wherein the selectable gene is flanked by site-specific resolvase sites.

5. The method of claim 3, wherein the selection medium comprises at least 75 μg/ml hygromycin.

6. The method of claim 1, wherein culturing the slow-growing mycobacterial strain characterized by clumping during culturing, followed by gravity sedimentation comprises culturing of the slow-growing mycobacterial strain in a medium containing a nonionic surfactant and/or emulsifier, followed by washing the cultured mycobacteria to remove the nonionic surfactant and/or emulsifier prior to culturing in the presence of the transducing mycobacteriophage.

7. The method of claim 6, wherein the nonionic surfactant and/or emulsifier comprises polysorbate 80.

8. The method of claim 1, wherein the target gene is at least one selected from the group of genes consisting of pknG, relA, lsr2, panC, panD, proC, trpD, sapM (MAP3432), lysA_1, leuD, and leuC.

9. The method of claim 1, wherein the allelic exchange frequency is at least 75% for a transduction frequency of $9.5 \times 10^{-8}$ to $1.6 \times 10^{-7}$.

10. The method of claim 1, further comprising confirmation of the allelic exchange mutants using at least one of polymerase chain reaction (PCR), nucleic acid sequencing, and RNA expression analysis.

11. A method for preparing a vaccine composition, comprising:

obtaining an allelic exchange mutant of a virulent slow-growing strain of mycobacteria by a method according to claim 1, wherein the allelic exchange mutant attenuates the virulence of the mycobacteria without eliminating the ability of the mycobacteria to sustain viability and colonize susceptible mammals; and suspending or dissolving the allelic exchange mutant in a pharmaceutical carrier of excipient to provide a live attenuated vaccine.

12. The method of claim 11, wherein the allelic exchange mutant is of *Mycobacterium avium* subsp. *paratuberculosis*, *M bovis* or *M. bovis* Bacille Calmette-Guérin (BCG), or *M. tuberculosis*.

13. A vaccine composition comprising a non-naturally occurring mycobacterial mutant prepared by the methods of claim 11, in a pharmaceutically acceptable carrier or excipient, wherein the vaccine is suitable to protect a mammal from challenge by a virulent *mycobacterium*.

14. The vaccine composition of claim 13, wherein the virulent *mycobacterium* is *Mycobacterium avium* subsp. *paratuberculosis* (Map), *M. bovis*, or *M. tuberculosis*.

15. The vaccine composition of claim 13, wherein the mammal is a cow, human, or human child.

16. The vaccine composition of claim 13, wherein the slow-growing strain of mycobacteria is *Mycobacterium avium* subsp. *paratuberculosis* (Map), Map K10, *Mycobacterium bovis*, or *Mycobacterium tuberculosis*.

17. The vaccine composition of claim 16, wherein the slow-growing strain of mycobacteria is *Mycobacterium avium* subsp. *paratuberculosis* (Map), and wherein the target gene is at least one selected from the group consisting of pknG, relA, lsr2, panC, panD, proC, trpD, sapM (MAP3432), lysA_1, leuD, and leuC.

18. The vaccine composition of claim 17, wherein the pknG, relA, lsr2, panC, panD, proC, trpD, sapM (MAP3432), lysA_1, leuD, and leuC genes comprise SEQ ID NOS:1, 4, 6, 34, 36, 38, 40, 42, 44, 46 and 48, contiguous portions thereof, or sequences at least 95%, at least 98%, or at least 99% identical thereto, respectively.

19. The vaccine composition of claim 13, wherein the vaccine comprises a live-attenuated vaccine.

20. The vaccine composition of claim 13, wherein the non-naturally occurring mycobacterial mutant strain further comprises a foreign DNA stably integrated its genomic DNA.

21. The vaccine composition of claim 20, wherein the foreign DNA encodes at least one protein or polypeptide selected from the group consisting of an antigen, an enzyme, a lymphokine, an immunopotentiator, and a reporter molecule.

22. The vaccine composition of claim 21, wherein the foreign DNA encodes at least one protein antigen selected from the group consisting of antigens from *Mycobacterium leprae*, *Mycobacterium tuberculosis*, malaria sporozoites, malaria merozoites, diphtheria toxoid, tetanus toxoids, *Leishmania* spp., *Salmonella* spp., *Mycobacterium africanum*, *Mycobacterium intracellulare*, *Mycobacterium avium*, *Treponema* spp., Pertussis, Herpes virus, Measles virus, Mumps virus, *Shigella* spp., *Neisseria* spp., *Borrelia* spp., rabies, polio virus, Human immunodeficiency virus, snake venom, insect venom, and *Vibrio cholera*; steroid enzymes; interleukins; tumor necrosis factor alpha and beta; interferon alpha, beta, and gamma; and reporter molecules GFP, luciferase, beta-galactosidase, beta-glucuronidase and catechol dehydrogenase.

23. The vaccine composition of claim 13, wherein protecting the mammal from challenge by a virulent *mycobacterium* comprises protecting the mammal from at least one of Johne' s disease, *paratuberculosis* (Ptb), Crohn's disease, or tuberculosis.

24. A non-naturally occurring allelic exchange mutant of a slow-growing strain of mycobacteria obtained according to the method of claim 1.

25. The non-naturally occurring allelic exchange mutant of claim 24, wherein the slow-growing strain of mycobacteria is *Mycobacterium avium*, *Mycobacterium avium* subsp. *paratuberculosis* (Map), Map K10, *Mycobacterium bovis*, or *Mycobacterium tuberculosis*.

26. The non-naturally occurring allelic exchange mutant of claim 25, wherein the *Mycobacterium avium* subsp. *paratuberculosis* (Map) is a GFP-expressing strain of Map K-10.

27. The non-naturally occurring allelic exchange mutant of claim 24, wherein the slow-growing strain of mycobacteria is *Mycobacterium avium* subsp. *paratuberculosis* (Map), and wherein the target gene is at least one selected from the group consisting of pknG, relA, lsr2, panC, panD, proC, trpD, sapM (MAP3432), lysA_1, leuD, and leuC.

28. A non-naturally occurring deletion mutant of *Mycobacterium avium* subsp. *paratuberculosis* (Map), wherein the Map exhibits attenuated virulence in a mammal when compared to the Map without the deletion, and wherein the target gene is at least one selected from the group consisting of pknG, relA, lsr2, panC, panD, proC, trpD, sapM (MAP3432), lysA_1, leuD, and leuC.

29. The non-naturally occurring deletion mutant of claim 28, wherein the target gene is at least one selected from the group consisting of pknG, relA, and lsr2.

30. The non-naturally occurring deletion mutant of claim 28, wherein the pknG, relA, lsr2, panC, panD, proC, trpD, sapM (MAP3432), lysA_1, leuD, and leuC genes comprise SEQ ID NOS:1, 4, 6, 34, 36, 38, 40, 42, 44, 46 and 48, contiguous portions thereof, or sequences at least 95%, at least 98%, or at least 99% identical thereto, respectively.

31. A method of protecting a mammal from a virulent *Mycobacterium avium* subsp. *paratuberculosis* (Map), *M. bovis*, or *M. tuberculosis*, comprising treating the mammal with the vaccine composition of claim 13.

32. The method of claim 31, wherein the vaccine composition is administered subcutaneously or intradermally.

33. A method of protecting a mammal from a virulent *Mycobacterium avium* subsp. *paratuberculosis* (Map), *M. bovis*, or *M. tuberculosis*, comprising treating the mammal with the deletion mutant of claim 28.

34. The method of claim 1, wherein, culturing the re-suspended slow-growing mycobacterial strain in the presence of the transducing mycobacteriophage at a non-permissive temperature to provide a mycobacteriophage-contacted culture further comprises depleting bacterial clumps in the mycobacteriophage-contacted culture by vigorously shaking the cultures, followed by low-speed centrifugation to provide a second low-speed mycobacteria pellet, and resuspending the second low-speed mycobacteria pellet in a culture medium or buffer.

* * * * *

SEQUENCE LISTING

```
<160> NUMBER OF SEQ ID NOS: 49

<210> SEQ ID NO 1
<211> LENGTH: 2292
<212> TYPE: DNA
<213> ORGANISM: Mycobacterium avium

<400> SEQUENCE: 1
tcagaacgtg ctggtgggtc gcaccttgtt ggccatgtcc accagcgcgt agcggtgccg      60
ctgggtgggg gcgacgcggg ccaggttgcg cagcgccgcc tcgacgccca gccgcagccc     120
gtgctcggtg aacgggaagc ccaggatgtg gttggtgctg gccttgttgt cctccagcca     180
gtccatcgcg cagccgagca ccagcgcgcg gatctgcaac acccgcggct cggtcggcgg     240
cagcgcctcc acccgccggg ccgcgtcccg gatttcctct tcggtgatct cgctcttgga     300
ccgcccggac aacagcgtca ccgcgctggt cagccgcgcg gtggtgaagt gccgcgaggt     360
ggccggcacc tcgtcgaggg tgcgcaccgc ggcggcccga tcaccctcgg cggacagggt     420
tctggccaat ccgaaggccg ccgagatcac gccgtcgttg gtcttccaca ccgtctcgta     480
gaaccggtgc tcgtcgacgt cgccggccag ctcggcggtc gcggccaacg ccaacttggg     540
cgccagctcg cccgggaagg tgtccagcac ctcggtgaaa tgcgttgtgg ccgaatcgta     600
gtcgccggtc agcagctcgg ccaccgcctt gtaccagacc agccgccact gccagccgac     660
ccgctcggcc aggtcgtcga gcttgcgggt ggccttggcc acgtcgccga ggtccagcag     720
cgcgcgcacc tccatcagcg gcagctcgat cgactcggac agctcgaccc cgtcggcgtc     780
cagcgtcccg tgccggcccg cgcgcagcga gtccagcgtc tgcaccggct gcgacaacac     840
cgtcgcctgc agcaccgggg cggcgacgtc ggccggatcg accagcggca cctgcagcgc     900
ggtcacgatc tcgcggcgg tcagcttctc cgaatgcacc tggccgtcca ggtacacgtc     960
ggtgtgcgcg accagcaggt cgaccccgaa cgtcgagcgg ctgggcgaga agatggtcga    1020
caggccgggc cgcggcaccc cggtgtcgtg cgcgaccacc tcgcgcagca cccccatcag    1080
ctgggccgac atctcctcgg tgctggagaa ccggcgccgc gggtcggggt cggtggcgcg    1140
gcgcagcaac cggcggaagg agtcgtaggt gcccagcacc gggtcgttgt cggggatgcc    1200
gtcgacgtag cggccgttgc gggtgggcag gttcagcgtg agcgcggcca gcgtgcgccc    1260
caccgtgtag atgtcggtgg ccaccgtcgg gccggtccgc acgatctccg gcgcctggaa    1320
acccggtgtg ccgtaaaggt atccgaacga gttgatccgc gacaccgcgc ccaggtcgat    1380
cagcttgagc tgctcctcgg tgagcatgat gttctccggc ttgaggtcgt tgtagaccag    1440
gccgatcgag tgcaggtaac ccagcgccgg cagtatctcc agcacgtagg cgatggcctc    1500
ggagacgggc agcttctcgc ccttgccgtg ccgcagcggc tgcccgccga cgtactccat    1560
```

```
gacgatgtag ccgaccggat tcccgtgccg gtccacatgc tcgacgaagt tgaagatctg    1620
cacgatctgc gggtgcacca cctcggcgag gaactgccgt tcggccatcg cgatggcctg    1680
cgcctcggcg tcaccggagt gcaccaggcc cttgagcacc accggccggt cgttgacgtt    1740
gtggtccacc gccaggtaga cccagcccag ccgccgtgc gcgatgcagc ccttgacctc     1800
gtactggttg gcgacgatgt cgcccggatt cagttgcggc agaaacgaat acgcgctgcc    1860
gcagtgcggg caccagccct cggaggtgcc cttgctcttc ttggtggacc gcccaccgg    1920 tttgccgcag ttccagcaga agcgcttgga ctccggcacc accgggttgg tcatcagcgc    1980
ctcgcgcggg tcgatgtcgc ggccgcgcgg aatctcgacc agcccaccgc cgagctgacg    2040
gaccggcggc agcgcctgcg tcgccaccgt catgcggtcg gcgctgtcgg tgtccagggc    2100
acccagcgag atgtgcggga agtcgtcgtc gtcatcgtcg aagtcgggcc ggaacagcgc    2160
ctgggtggcc tgcagccgcc cggttgccgc gccggcctgg gcgtcgtcgc ccacctcggc    2220
cggctgggtg cccgggccca tctgctcggc ccccggttcc ggctgctcgc tcttgttgtc    2280
cggctcggcc at                                                        2292
```

<210> SEQ ID NO 2
<211> LENGTH: 763
<212> TYPE: PRT
<213> ORGANISM: Mycobacterium avium

<400> SEQUENCE: 2

```
Met Ala Glu Pro Asp Asn Lys Ser Glu Gln Pro Glu Pro Gly Ala Glu
1               5                   10                  15

Gln Met Gly Pro Gly Thr Gln Pro Ala Glu Val Gly Asp Asp Ala Gln
            20                  25                  30

Ala Gly Ala Ala Thr Gly Arg Leu Gln Ala Thr Gln Ala Leu Phe Arg
        35                  40                  45

Pro Asp Phe Asp Asp Asp Asp Asp Phe Pro His Ile Ser Leu Gly
    50                  55                  60

Ala Leu Asp Thr Asp Ser Ala Asp Arg Met Thr Val Ala Thr Gln Ala
65                  70                  75                  80

Leu Pro Pro Val Arg Gln Leu Gly Gly Gly Leu Val Glu Ile Pro Arg
                85                  90                  95

Gly Arg Asp Ile Asp Pro Arg Glu Ala Leu Met Thr Asn Pro Val Val
            100                 105                 110

Pro Glu Ser Lys Arg Phe Cys Trp Asn Cys Gly Lys Pro Val Gly Arg
        115                 120                 125

Ser Thr Lys Lys Ser Lys Gly Thr Ser Glu Gly Trp Cys Pro His Cys
    130                 135                 140

Gly Ser Ala Tyr Ser Phe Leu Pro Gln Leu Asn Pro Gly Asp Ile Val
145                 150                 155                 160

Ala Asn Gln Tyr Glu Val Lys Gly Cys Ile Ala His Gly Gly Leu Gly
                165                 170                 175

Trp Val Tyr Leu Ala Val Asp His Asn Val Asn Asp Arg Pro Val Val
            180                 185                 190

Leu Lys Gly Leu Val His Ser Gly Asp Ala Glu Ala Gln Ala Ile Ala
        195                 200                 205

Met Ala Glu Arg Gln Phe Leu Ala Glu Val Val His Pro Gln Ile Val
    210                 215                 220

Gln Ile Phe Asn Phe Val Glu His Val Asp Arg His Gly Asn Pro Val
225                 230                 235                 240
```

```
Gly Tyr Ile Val Met Glu Tyr Val Gly Gly Gln Pro Leu Arg His Gly
                245                 250                 255

Lys Gly Glu Lys Leu Pro Val Ser Glu Ala Ile Ala Tyr Val Leu Glu
            260                 265                 270

Ile Leu Pro Ala Leu Gly Tyr Leu His Ser Ile Gly Leu Val Tyr Asn
        275                 280                 285

Asp Leu Lys Pro Glu Asn Ile Met Leu Thr Glu Glu Gln Leu Lys Leu
    290                 295                 300

Ile Asp Leu Gly Ala Val Ser Arg Ile Asn Ser Phe Gly Tyr Leu Tyr
305                 310                 315                 320

Gly Thr Pro Gly Phe Gln Ala Pro Glu Ile Val Arg Thr Gly Pro Thr
                325                 330                 335

Val Ala Thr Asp Ile Tyr Thr Val Gly Arg Thr Leu Ala Ala Leu Thr
            340                 345                 350

Leu Asn Leu Pro Thr Arg Asn Gly Arg Tyr Val Asp Gly Ile Pro Asp
        355                 360                 365

Asn Asp Pro Val Leu Gly Thr Tyr Asp Ser Phe Arg Arg Leu Leu Arg
    370                 375                 380

Arg Ala Thr Asp Pro Asp Pro Arg Arg Phe Ser Ser Thr Glu Glu
385                 390                 395                 400

Met Ser Ala Gln Leu Met Gly Val Leu Arg Glu Val Val Ala His Asp
                405                 410                 415

Thr Gly Val Pro Arg Pro Gly Leu Ser Thr Ile Phe Ser Pro Ser Arg
            420                 425                 430

Ser Thr Phe Gly Val Asp Leu Leu Val Ala His Thr Asp Val Tyr Leu
        435                 440                 445

Asp Gly Gln Val His Ser Glu Lys Leu Thr Ala Arg Glu Ile Val Thr
    450                 455                 460

Ala Leu Gln Val Pro Leu Val Asp Pro Ala Asp Val Ala Ala Pro Val
465                 470                 475                 480

Leu Gln Ala Thr Val Leu Ser Gln Pro Val Gln Thr Leu Asp Ser Leu
                485                 490                 495

Arg Ala Ala Arg His Gly Thr Leu Asp Ala Asp Gly Val Glu Leu Ser
            500                 505                 510

Glu Ser Ile Glu Leu Pro Leu Met Glu Val Arg Ala Leu Leu Asp Leu
        515                 520                 525

Gly Asp Val Ala Lys Ala Thr Arg Lys Leu Asp Asp Leu Ala Glu Arg
    530                 535                 540

Val Gly Trp Gln Trp Arg Leu Val Trp Tyr Lys Ala Val Ala Glu Leu
545                 550                 555                 560

Leu Thr Gly Asp Tyr Asp Ser Ala Thr Thr His Phe Thr Glu Val Leu
                565                 570                 575

Asp Thr Phe Pro Gly Glu Leu Ala Pro Lys Leu Ala Leu Ala Ala Thr
            580                 585                 590

Ala Glu Leu Ala Gly Asp Val Asp Glu His Arg Phe Tyr Glu Thr Val
        595                 600                 605

Trp Lys Thr Asn Asp Gly Val Ile Ser Ala Ala Phe Gly Leu Ala Arg
    610                 615                 620

Thr Leu Ser Ala Glu Gly Asp Arg Ala Ala Val Arg Thr Leu Asp
625                 630                 635                 640

Glu Val Pro Ala Thr Ser Arg His Phe Thr Thr Ala Arg Leu Thr Ser
                645                 650                 655

Ala Val Thr Leu Leu Ser Gly Arg Ser Lys Ser Glu Ile Thr Glu Glu
```

```
                    660                 665                 670
Glu Ile Arg Asp Ala Ala Arg Arg Val Glu Ala Leu Pro Pro Thr Glu
                675                 680                 685

Pro Arg Val Leu Gln Ile Arg Ala Leu Val Leu Gly Cys Ala Met Asp
            690                 695                 700

Trp Leu Glu Asp Asn Lys Ala Ser Thr Asn His Ile Leu Gly Phe Pro
705                 710                 715                 720

Phe Thr Glu His Gly Leu Arg Leu Gly Val Glu Ala Ala Leu Arg Asn
                725                 730                 735

Leu Ala Arg Val Ala Pro Thr Gln Arg His Arg Tyr Ala Leu Val Asp
            740                 745                 750

Met Ala Asn Lys Val Arg Pro Thr Ser Thr Phe
                755                 760
```

<210> SEQ ID NO 3
<211> LENGTH: 309
<212> TYPE: PRT
<213> ORGANISM: Mycobacterium avium

<400> SEQUENCE: 3

```
Met Leu Val Ala Ala Gly Cys Gly His Thr Glu Ser Leu Arg Val Ala
1               5                   10                  15

Ser Val Pro Thr Leu Pro Pro Thr Pro Val Gly Met Glu Gln Leu
            20                  25                  30

Pro Pro Gln Pro Pro Leu Pro Pro Asp Gly Pro Asp Gln Asn Cys Asp
                35                  40                  45

Leu Thr Ala Ser Leu Arg Pro Phe Pro Thr Lys Ala Glu Ala Asp Ala
            50                  55                  60

Ala Val Ala Asp Ile Arg Ala Arg Gly Arg Leu Ile Val Gly Leu Asp
65                  70                  75                  80

Ile Gly Ser Asn Leu Phe Ser Phe Arg Asp Pro Ile Thr Gly Glu Ile
                85                  90                  95

Thr Gly Phe Asp Val Asp Ile Ala Gly Glu Ile Ala Arg Asp Ile Phe
            100                 105                 110

Gly Ala Pro Ser His Val Glu Tyr Arg Ile Leu Ser Ser Asp Glu Arg
                115                 120                 125

Val Thr Ala Leu Gln Arg Gly Glu Val Asp Val Val Lys Thr Met
            130                 135                 140

Thr Ile Thr Cys Asp Arg Arg Lys Gln Val Asn Phe Ser Thr Val Tyr
145                 150                 155                 160

Leu Asp Ala Asn Gln Arg Ile Leu Ala Pro Arg Asp Ser Pro Ile Thr
                165                 170                 175

Lys Val Ser Asp Leu Ser Gly Lys Arg Val Cys Val Ala Lys Gly Thr
            180                 185                 190

Thr Ser Leu His Arg Ile Arg Gln Ile Asp Pro Pro Ile Val Val
                195                 200                 205

Ser Val Val Asn Trp Ala Asp Cys Leu Val Ala Met Gln Gln Arg Glu
            210                 215                 220

Ile Asp Ala Val Ser Thr Asp Ser Ile Leu Ala Gly Leu Val Glu
225                 230                 235                 240

Glu Asp Pro Tyr Leu His Ile Val Gly Pro Asn Met Ala Thr Gln Pro
                245                 250                 255

Tyr Gly Ile Gly Ile Asn Leu Asn Asn Thr Gly Leu Val Arg Phe Val
            260                 265                 270
```

Asn Gly Thr Leu Glu Arg Ile Arg Arg Asp Gly Thr Trp Asn Thr Leu
    275                 280                 285

Tyr Arg Lys Trp Leu Thr Val Leu Gly Pro Ala Pro Ala Pro Pro Thr
    290                 295                 300

Pro Arg Tyr Leu Asp
305

<210> SEQ ID NO 4
<211> LENGTH: 2367
<212> TYPE: DNA
<213> ORGANISM: Mycobacterium avium

<400> SEQUENCE: 4

| | | | | | |
|---|---|---|---|---|---|
| gtggcggagg | aaaacagcgc | ggcgcaagcg | cttgacgcgc | cggcggagtc | gccgcccaac | 60 |
| ccggtgatcg | agactcccga | gccgccgacc | gaatcgctca | agacgtccag | cagcgcgtcg | 120 |
| cgccgggtcc | gggcccggct | ggcccggcgg | atgaccgccc | agcgcagcac | gctcaacccg | 180 |
| gtgctggagc | cgctggtggc | gatgcaccgc | gagatctacc | ccaaggccaa | cgtgcagctg | 240 |
| ctgcagcgcg | cattcgaggt | cgccgaccag | cggcacgcca | gccagttgcg | ccactccggc | 300 |
| gaccectaca | tcacccatcc | gctggccgtc | gccaccatcc | tggccgaatt | gggcatggac | 360 |
| accaccactt | tggtggccgc | gctgttgcac | gacaccgtcg | aggacaccgg | ctacaccctg | 420 |
| gcccagctgt | ccgaggaatt | cggcgaagag | gtcggtcatc | tggtcgacgg | ggtgaccaag | 480 |
| ctggaccggg | tggtgctggg | cagcgccgcc | gagggcgaga | ccatccgcaa | gatgatcacc | 540 |
| gcgatggccc | gcgacccgcg | ggtgctggtg | atcaaggtcg | ccgaccggct | gcacaacatg | 600 |
| cgcaccatgc | ggttcctgcc | gccggagaag | caggcccgca | aggcccgcga | cgctggaa | 660 |
| gtcattgcgc | cctcgccca | tcggctgggc | atggccagcg | tcaagtggga | gttggaggac | 720 |
| ctgtcgttcg | ccatcctgca | tcccaagaag | tacgacgaga | tcgtccggct | ggtcgccggc | 780 |
| cgggcccccgt | cgcgggacac | ctacctggcc | aaggtgcggg | ccgagatcat | caacacgctg | 840 |
| aacgcgtcga | agatcaaggc | gacggtggag | ggccggccca | agcactactg | gtcgatctac | 900 |
| cagaagatga | tcgtcaaggg | ccgcgacttc | gacgacatcc | acgacctggt | cggcatccgc | 960 |
| atcctgtgcg | acgagatccg | ggactgctat | gccgctgtgg | gcgtggtgca | ttcgctgtgg | 1020 |
| cagccgatgg | ccgggcggtt | caaggactac | atcgcccagc | cgcgctacgg | cgtctaccag | 1080 |
| tcgctgcaca | ccaccgtcgt | cgggccgag | ggcaagccgc | tggaggtgca | gatccgcacc | 1140 |
| cgcgacatgc | accgcaccgc | cgagtacggc | atcgccgcgc | actggcgcta | caaggaagcc | 1200 |
| aagggccgca | acggcgttcc | gcacccgcac | gccgccgccg | agatcgacga | catggcctgg | 1260 |
| atgcgccagc | tgctcgactg | gcagcgggaa | gccgccgacc | cgggcgaatt | cctcgagtcg | 1320 |
| ctgcgctatg | accttgcggt | acaagagatc | ttcgtgttca | cccccaaggg | cgacgtgatc | 1380 |
| accctgcccc | ccgggtcgac | gccgatcgac | ttcgcctatg | ccgtgcacac | cgaggtcggg | 1440 |
| caccgctgca | tcgcgcccg | ggtcaacggc | cggctggtgg | cgctgaacg | caagctggaa | 1500 |
| aacggggaag | tcgtcgaggt | tttcacctcc | aaggcggcca | cgcgggccc | gtcgcgggac | 1560 |
| tggcagcagt | tcgtggtgtc | gccgcgggcc | aaggccaaga | tccggcagtg | gttcgccaag | 1620 |
| gagcggcgcg | aggaggccct | ggaggccggc | aaggacgcga | tggcccgcga | ggtgcgccgc | 1680 |
| ggcggacttc | cgttgcagcg | cttggtcaat | gccgaatcca | tgagcgcggt | ggcccgcgaa | 1740 |
| ctgcactacg | ccgacgtgtc | ggccctctac | accgcgatcg | gtgaggggca | tgtgtcggcc | 1800 |
| cggcacgtgg | tgcagcggct | gctggccgag | ctcggcggca | tcgaccagac | cgaggaggac | 1860 |

-continued

```
ctcgccgagc ggtccacccc gaccaccatg ctgcgccgcc cgcgcagcag cgacgacgtc    1920
ggcgtgtcgg tgcccggcgc cccgggcgtg ctgaccaagc tggccaaatg ctgcacgccg    1980
gtgcctgggg accagatcat gggattcgtc acccgcggcg gcggggtgag cgtgcaccgc    2040
accgactgca ccaacgccgc ctcgctgcag cagcagtccg agcgcatcat cgaggtgcac    2100
tgggcgccgt cgccgtcgtc ggtgttcctg gtggccattc aggtcgaggc gctcgaccgg    2160
caccggctgt tgtccgacgt cacccgggtg ctggccgacg agaaggtcaa catcctgtcc    2220
gcgtcggtca ccacctccgg tgaccgggtt gccatcagcc gcttcaccctt tgagatgggg    2280 gaccccaagc acctcggcca cctgctcaac gtggtgcgca acgtcgaagg cgtctacgac    2340
gtctaccggg tgacctccgc cgcctga                                         2367
```

<210> SEQ ID NO 5
<211> LENGTH: 788
<212> TYPE: PRT
<213> ORGANISM: Mycobacterium avium

<400> SEQUENCE: 5

```
Met Ala Glu Glu Asn Ser Ala Ala Gln Ala Leu Asp Ala Pro Ala Glu
1               5                   10                  15

Ser Pro Pro Asn Pro Val Ile Glu Thr Pro Glu Pro Pro Thr Glu Ser
            20                  25                  30

Leu Lys Thr Ser Ser Ser Ala Ser Arg Val Arg Ala Arg Leu Ala
        35                  40                  45

Arg Arg Met Thr Ala Gln Arg Ser Thr Leu Asn Pro Val Leu Glu Pro
    50                  55                  60

Leu Val Ala Met His Arg Glu Ile Tyr Pro Lys Ala Asn Val Gln Leu
65                  70                  75                  80

Leu Gln Arg Ala Phe Glu Val Ala Asp Gln Arg His Ala Ser Gln Leu
                85                  90                  95

Arg His Ser Gly Asp Pro Tyr Ile Thr His Pro Leu Ala Val Ala Thr
            100                 105                 110

Ile Leu Ala Glu Leu Gly Met Asp Thr Thr Thr Leu Val Ala Ala Leu
        115                 120                 125

Leu His Asp Thr Val Glu Asp Thr Gly Tyr Thr Leu Ala Gln Leu Ser
    130                 135                 140

Glu Glu Phe Gly Glu Val Gly His Leu Val Asp Gly Val Thr Lys
145                 150                 155                 160

Leu Asp Arg Val Val Leu Gly Ser Ala Ala Glu Gly Glu Thr Ile Arg
                165                 170                 175

Lys Met Ile Thr Ala Met Ala Arg Asp Pro Arg Val Leu Val Ile Lys
            180                 185                 190

Val Ala Asp Arg Leu His Asn Met Arg Thr Met Arg Phe Leu Pro Pro
        195                 200                 205

Glu Lys Gln Ala Arg Lys Ala Arg Glu Thr Leu Glu Val Ile Ala Pro
    210                 215                 220

Leu Ala His Arg Leu Gly Met Ala Ser Val Lys Trp Glu Leu Glu Asp
225                 230                 235                 240

Leu Ser Phe Ala Ile Leu His Pro Lys Lys Tyr Asp Glu Ile Val Arg
                245                 250                 255

Leu Val Ala Gly Arg Ala Pro Ser Arg Asp Thr Tyr Leu Ala Lys Val
            260                 265                 270

Arg Ala Glu Ile Ile Asn Thr Leu Asn Ala Ser Lys Ile Lys Ala Thr
        275                 280                 285
```

```
Val Glu Gly Arg Pro Lys His Tyr Trp Ser Ile Tyr Gln Lys Met Ile
    290                 295                 300

Val Lys Gly Arg Asp Phe Asp Asp Ile His Asp Leu Val Gly Ile Arg
305                 310                 315                 320

Ile Leu Cys Asp Glu Ile Arg Asp Cys Tyr Ala Ala Val Gly Val Val
                325                 330                 335

His Ser Leu Trp Gln Pro Met Ala Gly Arg Phe Lys Asp Tyr Ile Ala
                340                 345                 350

Gln Pro Arg Tyr Gly Val Tyr Gln Ser Leu His Thr Val Val Gly
                355                 360                 365

Pro Glu Gly Lys Pro Leu Glu Val Gln Ile Arg Thr Arg Asp Met His
    370                 375                 380

Arg Thr Ala Glu Tyr Gly Ile Ala Ala His Trp Arg Tyr Lys Glu Ala
385                 390                 395                 400

Lys Gly Arg Asn Gly Val Pro His Pro His Ala Ala Ala Glu Ile Asp
                405                 410                 415

Asp Met Ala Trp Met Arg Gln Leu Leu Asp Trp Gln Arg Glu Ala Ala
                420                 425                 430

Asp Pro Gly Glu Phe Leu Glu Ser Leu Arg Tyr Asp Leu Ala Val Gln
                435                 440                 445

Glu Ile Phe Val Phe Thr Pro Lys Gly Asp Val Ile Thr Leu Pro Thr
    450                 455                 460

Gly Ser Thr Pro Ile Asp Phe Ala Tyr Ala Val His Thr Glu Val Gly
465                 470                 475                 480

His Arg Cys Ile Gly Ala Arg Val Asn Gly Arg Leu Val Ala Leu Glu
                485                 490                 495

Arg Lys Leu Glu Asn Gly Glu Val Val Glu Val Phe Thr Ser Lys Ala
                500                 505                 510

Ala Asn Ala Gly Pro Ser Arg Asp Trp Gln Gln Phe Val Val Ser Pro
                515                 520                 525

Arg Ala Lys Ala Lys Ile Arg Gln Trp Phe Ala Lys Glu Arg Arg Glu
    530                 535                 540

Glu Ala Leu Glu Ala Gly Lys Asp Ala Met Ala Arg Glu Val Arg Arg
545                 550                 555                 560

Gly Gly Leu Pro Leu Gln Arg Leu Val Asn Ala Glu Ser Met Ser Ala
                565                 570                 575

Val Ala Arg Glu Leu His Tyr Ala Asp Val Ser Ala Leu Tyr Thr Ala
                580                 585                 590

Ile Gly Glu Gly His Val Ser Ala Arg His Val Val Gln Arg Leu Leu
                595                 600                 605

Ala Glu Leu Gly Gly Ile Asp Gln Thr Glu Glu Asp Leu Ala Glu Arg
    610                 615                 620

Ser Thr Pro Thr Thr Met Leu Arg Arg Pro Arg Ser Ser Asp Asp Val
625                 630                 635                 640

Gly Val Ser Val Pro Gly Ala Pro Gly Val Leu Thr Lys Leu Ala Lys
                645                 650                 655

Cys Cys Thr Pro Val Pro Gly Asp Gln Ile Met Gly Phe Val Thr Arg
                660                 665                 670

Gly Gly Gly Val Ser Val His Arg Thr Asp Cys Thr Asn Ala Ala Ser
                675                 680                 685

Leu Gln Gln Gln Ser Glu Arg Ile Ile Glu Val His Trp Ala Pro Ser
    690                 695                 700
```

```
Pro Ser Ser Val Phe Leu Val Ala Ile Gln Val Glu Ala Leu Asp Arg
705                 710                 715                 720

His Arg Leu Leu Ser Asp Val Thr Arg Val Leu Ala Asp Glu Lys Val
                725                 730                 735

Asn Ile Leu Ser Ala Ser Val Thr Thr Ser Gly Asp Arg Val Ala Ile
            740                 745                 750

Ser Arg Phe Thr Phe Glu Met Gly Asp Pro Lys His Leu Gly His Leu
        755                 760                 765

Leu Asn Val Val Arg Asn Val Glu Gly Val Tyr Asp Val Tyr Arg Val
    770                 775                 780

Thr Ser Ala Ala
785

<210> SEQ ID NO 6
<211> LENGTH: 339
<212> TYPE: DNA
<213> ORGANISM: Mycobacterium avium

<400> SEQUENCE: 6
atggcaaaaa aagtgaccgt caccttggtc gatgatttcg acggtgccgg cgcagccgac        60
gaaacagtgg aattcgggct tgacggggtg acctacgaga ttgacctttc gtccaagaat       120
gccgcgaaac ttcgtaatga tctgaagcaa tgggtggaag ccggccgtcg cgtcggcggc       180
cgccggcgcg ggcgctcggg ctcgggacgc ggccgcggcg ccatcgaccg cgagcagagc       240
gcggcgatcc gcgaatgggc ccgtcgcaac gggcacaacg tgtcgacccg cggccgcatc       300
ccggccgacg tcatcgacgc cttccacgcc gcaacctga                              339

<210> SEQ ID NO 7
<211> LENGTH: 112
<212> TYPE: PRT
<213> ORGANISM: Mycobacterium avium

<400> SEQUENCE: 7

Met Ala Lys Lys Val Thr Val Thr Leu Val Asp Asp Phe Asp Gly Ala
1               5                   10                  15

Gly Ala Ala Asp Glu Thr Val Glu Phe Gly Leu Asp Gly Val Thr Tyr
            20                  25                  30

Glu Ile Asp Leu Ser Ser Lys Asn Ala Ala Lys Leu Arg Asn Asp Leu
        35                  40                  45

Lys Gln Trp Val Glu Ala Gly Arg Val Gly Arg Arg Gly
    50                  55                  60

Arg Ser Gly Ser Gly Arg Gly Arg Gly Ala Ile Asp Arg Glu Gln Ser
65                  70                  75                  80

Ala Ala Ile Arg Glu Trp Ala Arg Arg Asn Gly His Asn Val Ser Thr
                85                  90                  95

Arg Gly Arg Ile Pro Ala Asp Val Ile Asp Ala Phe His Ala Ala Thr
            100                 105                 110

<210> SEQ ID NO 8
<211> LENGTH: 21
<212> TYPE: DNA
<213> ORGANISM: Artificial
<220> FEATURE:
<223> OTHER INFORMATION: pknGU-F primer

<400> SEQUENCE: 8
tcgtggtgtc ggtggtcaac t                                                  21
```

```
<210> SEQ ID NO 9
<211> LENGTH: 21
<212> TYPE: DNA
<213> ORGANISM: Artificial
<220> FEATURE:
<223> OTHER INFORMATION: pknGU-R primer

<400> SEQUENCE: 9
gcccttgctc ttcttggtgg a                                               21

<210> SEQ ID NO 10
<211> LENGTH: 22
<212> TYPE: DNA
<213> ORGANISM: Artificial
<220> FEATURE:
<223> OTHER INFORMATION: pknGD-F primer

<400> SEQUENCE: 10
cacatcctgg gcttcccgtt ca                                              22

<210> SEQ ID NO 11
<211> LENGTH: 22
<212> TYPE: DNA
<213> ORGANISM: Artificial
<220> FEATURE:
<223> OTHER INFORMATION: pknGD-R primer

<400> SEQUENCE: 11
tacctgcggc tgctgctcat cg                                              22

<210> SEQ ID NO 12
<211> LENGTH: 22
<212> TYPE: DNA
<213> ORGANISM: Artificial
<220> FEATURE:
<223> OTHER INFORMATION: lsr2U-F primer

<400> SEQUENCE: 12
tagaaatgta cccgtcgctg tc                                              22

<210> SEQ ID NO 13
<211> LENGTH: 20
<212> TYPE: DNA
<213> ORGANISM: Artificial
<220> FEATURE:
<223> OTHER INFORMATION: lsr2U-R primer

<400> SEQUENCE: 13
tttgccattg gcttaccctc                                                 20

<210> SEQ ID NO 14
<211> LENGTH: 18
<212> TYPE: DNA
<213> ORGANISM: Artificial
<220> FEATURE:
<223> OTHER INFORMATION: lsr2D-F primer

<400> SEQUENCE: 14
ccttccacgc cgcaacct                                                   18

<210> SEQ ID NO 15
<211> LENGTH: 20
<212> TYPE: DNA
<213> ORGANISM: Artificial
<220> FEATURE:
<223> OTHER INFORMATION: lsr2D-R primer
```

```
<400> SEQUENCE: 15
ggctcagctc cagcaccttc                                              20

<210> SEQ ID NO 16
<211> LENGTH: 20
<212> TYPE: DNA
<213> ORGANISM: Artificial
<220> FEATURE:
<223> OTHER INFORMATION: relASU-F primer

<400> SEQUENCE: 16
cgaccgaatc gctcaagacg                                              20

<210> SEQ ID NO 17
<211> LENGTH: 21
<212> TYPE: DNA
<213> ORGANISM: Artificial
<220> FEATURE:
<223> OTHER INFORMATION: relASU-R primer

<400> SEQUENCE: 17
gcgaacgaca ggtcctccaa c                                            21

<210> SEQ ID NO 18
<211> LENGTH: 19
<212> TYPE: DNA
<213> ORGANISM: Artificial
<220> FEATURE:
<223> OTHER INFORMATION: relASD-F primer

<400> SEQUENCE: 18
gcagtggttc gccaaggag                                               19

<210> SEQ ID NO 19
<211> LENGTH: 19
<212> TYPE: DNA
<213> ORGANISM: Artificial
<220> FEATURE:
<223> OTHER INFORMATION: relASD-R primer

<400> SEQUENCE: 19
gggtcgccca tctcaaagg                                               19

<210> SEQ ID NO 20
<211> LENGTH: 21
<212> TYPE: DNA
<213> ORGANISM: Artificial
<220> FEATURE:
<223> OTHER INFORMATION: relALU-F primer

<400> SEQUENCE: 20
aagaagatgt acgcggtgag c                                            21

<210> SEQ ID NO 21
<211> LENGTH: 18
<212> TYPE: DNA
<213> ORGANISM: Artificial
<220> FEATURE:
<223> OTHER INFORMATION: relALU-R primer

<400> SEQUENCE: 21
cttgagcgat tcggtcgg                                                18

<210> SEQ ID NO 22
```

```
<211> LENGTH: 21
<212> TYPE: DNA
<213> ORGANISM: Artificial
<220> FEATURE:
<223> OTHER INFORMATION: relALD-F primer

<400> SEQUENCE: 22
atcgaccaga ccgaggagga c                                              21

<210> SEQ ID NO 23
<211> LENGTH: 19
<212> TYPE: DNA
<213> ORGANISM: Artificial
<220> FEATURE:
<223> OTHER INFORMATION: relALD-R primer

<400> SEQUENCE: 23
ccacagacca acggcaagg                                                 19

<210> SEQ ID NO 24
<211> LENGTH: 20
<212> TYPE: DNA
<213> ORGANISM: Artificial
<220> FEATURE:
<223> OTHER INFORMATION: delta relAS primer relL-3F

<400> SEQUENCE: 24
ttcggaggtg agcatcgtgg                                                20

<210> SEQ ID NO 25
<211> LENGTH: 20
<212> TYPE: DNA
<213> ORGANISM: Artificial
<220> FEATURE:
<223> OTHER INFORMATION: delta relAS primer relR-3R

<400> SEQUENCE: 25
ccgacaacgg gtcctgctac                                                20

<210> SEQ ID NO 26
<211> LENGTH: 18
<212> TYPE: DNA
<213> ORGANISM: Artificial
<220> FEATURE:
<223> OTHER INFORMATION: delta lsr2 primer lsrL-1F

<400> SEQUENCE: 26
ccccaatgtt gcagacgc                                                  18

<210> SEQ ID NO 27
<211> LENGTH: 19
<212> TYPE: DNA
<213> ORGANISM: Artificial
<220> FEATURE:
<223> OTHER INFORMATION: delta lsr2 primer lsrR-1R

<400> SEQUENCE: 27
tcacccgctc gatttcctt                                                 19

<210> SEQ ID NO 28
<211> LENGTH: 21
<212> TYPE: DNA
<213> ORGANISM: Artificial
<220> FEATURE:
<223> OTHER INFORMATION: left side of delta pknG; primer pknL-1F

<400> SEQUENCE: 28
```

```
accagaactg cgacctgacg g                                          21
```

<210> SEQ ID NO 29
<211> LENGTH: 20
<212> TYPE: DNA
<213> ORGANISM: Artificial
<220> FEATURE:
<223> OTHER INFORMATION: hyg-R primer

<400> SEQUENCE: 29

```
gccctacctg gtgatgagcc                                            20
```

<210> SEQ ID NO 30
<211> LENGTH: 20
<212> TYPE: DNA
<213> ORGANISM: Artificial
<220> FEATURE:
<223> OTHER INFORMATION: right side of delta pknG; primer hyg-F

<400> SEQUENCE: 30

```
cacgaagatg ttggtcccgt                                            20
```

<210> SEQ ID NO 31
<211> LENGTH: 20
<212> TYPE: DNA
<213> ORGANISM: Artificial
<220> FEATURE:
<223> OTHER INFORMATION: pknR-1R

<400> SEQUENCE: 31

```
tccaccacaa cactcgtgcc                                            20
```

<210> SEQ ID NO 32
<211> LENGTH: 19
<212> TYPE: DNA
<213> ORGANISM: Artificial
<220> FEATURE:
<223> OTHER INFORMATION: left side of delta relAL; primer relL-1F

<400> SEQUENCE: 32

```
caggtggaca acgcgatcg                                             19
```

<210> SEQ ID NO 33
<211> LENGTH: 19
<212> TYPE: DNA
<213> ORGANISM: Artificial
<220> FEATURE:
<223> OTHER INFORMATION: relR2R primer

<400> SEQUENCE: 33

```
tgcgtcgttg atgagggtt                                             19
```

<210> SEQ ID NO 34
<211> LENGTH: 927
<212> TYPE: DNA
<213> ORGANISM: Mycobacterium avium

<400> SEQUENCE: 34

```
gtgaaacccg ccttcaccgc gggcgaactc aacacctaca ccagcccggg cgacgtcacc    60
gccgtcagcc gcgcgctgcg ccacaccggc cgccgggtga tgctggtgcc caccatgggt   120
gcgctgcacg acggccacct cgcgctggtg cgggcggcca agcgggtgcc cggttcggtg   180
gtggtggtgt cgatcttcgt caacccgctg caattcggcg ccggcgaaga cctggacgcc   240
```

-continued

```
taccccgca ccctggacga cgacctggcg ctgctgcgct ccgagggcgt cgaaatcgcc    300
ttcaccccaa cggccgcggc gatgtacccg aatggtttgc gcaccaccgt gcagcccggc    360
ccgctggccg ccgagctgga gggcgggccc cggccgacgc atttcgccgg cgtgctgacc    420
gtcgtgtgca agctgctgca gatcgtgcgc ccggaccgaa tcttcttcgg cgagaaggac    480
taccagcagc tggtgatgat ccgtcagatg gtcgccgacc tcaacatcga cgtgcaggtg    540
gtcggggtgc cgaccgtgcg ggaggccgac ggcctggcga tgtcgtcgcg caaccgctac    600
ctggacgcca cgcaacgcga actggccgtg acgctttcgg cggccctgac cgccggcgcg    660
cacgccgctc acctgggcgg tgcggccgcg ctgcgggccg cgcgggcggt gctggacgcc    720
gtgcccgagc tcaccgtcga ctatctcgag ctgcgcgacg ccgggctggg cccggcaccc    780
gcccacggct cggcgcggct gctggtcgcc gcccggctgg gcaacacccg actgctggat    840
aacatcgaaa tgcagatcga aacacccgcc ggcaccgctg ggccggacgg cgaccgccaa    900
tacgcccaat caccttggag gaattga                                        927
```

<210> SEQ ID NO 35
<211> LENGTH: 308
<212> TYPE: PRT
<213> ORGANISM: Mycobacterium avium

<400> SEQUENCE: 35

```
Met Lys Pro Ala Phe Thr Ala Gly Glu Leu Asn Thr Tyr Thr Ser Pro
1               5                   10                  15

Gly Asp Val Thr Ala Val Ser Arg Ala Leu Arg His Thr Gly Arg Arg
            20                  25                  30

Val Met Leu Val Pro Thr Met Gly Ala Leu His Asp Gly His Leu Ala
        35                  40                  45

Leu Val Arg Ala Ala Lys Arg Val Pro Gly Ser Val Val Val Val Ser
    50                  55                  60

Ile Phe Val Asn Pro Leu Gln Phe Gly Ala Gly Glu Asp Leu Asp Ala
65                  70                  75                  80

Tyr Pro Arg Thr Leu Asp Asp Asp Leu Ala Leu Leu Arg Ser Glu Gly
                85                  90                  95

Val Glu Ile Ala Phe Thr Pro Thr Ala Ala Ala Met Tyr Pro Asn Gly
            100                 105                 110

Leu Arg Thr Thr Val Gln Pro Gly Pro Leu Ala Ala Glu Leu Glu Gly
        115                 120                 125

Gly Pro Arg Pro Thr His Phe Ala Gly Val Leu Thr Val Val Cys Lys
    130                 135                 140

Leu Leu Gln Ile Val Arg Pro Asp Arg Ile Phe Phe Gly Glu Lys Asp
145                 150                 155                 160

Tyr Gln Gln Leu Val Met Ile Arg Gln Met Val Ala Asp Leu Asn Ile
                165                 170                 175

Asp Val Gln Val Val Gly Val Pro Thr Val Arg Glu Ala Asp Gly Leu
            180                 185                 190

Ala Met Ser Ser Arg Asn Arg Tyr Leu Asp Ala Thr Gln Arg Glu Leu
        195                 200                 205

Ala Val Thr Leu Ser Ala Ala Leu Thr Ala Gly Ala His Ala Ala His
    210                 215                 220

Leu Gly Gly Ala Ala Ala Leu Arg Ala Ala Arg Ala Val Leu Asp Ala
225                 230                 235                 240

Val Pro Glu Leu Thr Val Asp Tyr Leu Glu Leu Arg Asp Ala Gly Leu
                245                 250                 255
```

Gly Pro Ala Pro Ala His Gly Ser Ala Arg Leu Leu Val Ala Ala Arg
            260                 265                 270

Leu Gly Asn Thr Arg Leu Leu Asp Asn Ile Glu Met Gln Ile Glu Thr
        275                 280                 285

Pro Ala Gly Thr Ala Gly Pro Asp Gly Asp Arg Gln Tyr Ala Gln Ser
    290                 295                 300

Pro Trp Arg Asn
305

<210> SEQ ID NO 36
<211> LENGTH: 432
<212> TYPE: DNA
<213> ORGANISM: Mycobacterium avium

<400> SEQUENCE: 36
atgttacgga cgatgctcaa gtcgaagatc accgggcca ccgtcacgca ggccgacctg      60
cactacgtgg ctcggtgac catcgacgcc gacctgatgg acgccgccga cctgctcgag     120
ggcgaacagg tgaccatcgt cgacatcgac aacggcgccc ggctggtcac ctacgcgatc    180
accggtgagc gtggcagcgg ggtgatcggg atcaacggtg ccgcagcgca tctggtccac    240
ccgggcgatc tggtcatcct gatcgcgtat ggaccatgg aggaggccga ggcgcgggcg     300
tatcagccgc gaatcgtctt cgtcgacgcc gacaacaagc cggtcgacct cggccacgat    360
ccggcattcg tgccggactt cgagatagca ggggcggccg agctgctcga tccccggatc    420
gttgcgcggt ag                                                        432

<210> SEQ ID NO 37
<211> LENGTH: 143
<212> TYPE: PRT
<213> ORGANISM: Mycobacterium avium

<400> SEQUENCE: 37

Met Leu Arg Thr Met Leu Lys Ser Lys Ile His Arg Ala Thr Val Thr
1               5                   10                  15

Gln Ala Asp Leu His Tyr Val Gly Ser Val Thr Ile Asp Ala Asp Leu
            20                  25                  30

Met Asp Ala Ala Asp Leu Leu Glu Gly Glu Gln Val Thr Ile Val Asp
        35                  40                  45

Ile Asp Asn Gly Ala Arg Leu Val Thr Tyr Ala Ile Thr Gly Glu Arg
    50                  55                  60

Gly Ser Gly Val Ile Gly Ile Asn Gly Ala Ala Ala His Leu Val His
65                  70                  75                  80

Pro Gly Asp Leu Val Ile Leu Ile Ala Tyr Gly Thr Met Glu Glu Ala
                85                  90                  95

Glu Ala Arg Ala Tyr Gln Pro Arg Ile Val Phe Val Asp Ala Asp Asn
            100                 105                 110

Lys Pro Val Asp Leu Gly His Asp Pro Ala Phe Val Pro Asp Phe Glu
        115                 120                 125

Ile Ala Gly Ala Ala Glu Leu Leu Asp Pro Arg Ile Val Ala Arg
    130                 135                 140

<210> SEQ ID NO 38
<211> LENGTH: 897
<212> TYPE: DNA
<213> ORGANISM: Mycobacterium avium

<400> SEQUENCE: 38

```
gtgtctgcga tgctgtccgg catggcaaga atcgcaatca tcggtggcgg cagcatcggg     60
gaggccctgc tgtcgggtct gctgcgggcg ggccggcagg tcaaggacct ggtggtggtc    120
gagcgggttc ccgagcgcgc caaatatctg gccgacacct actcggtgct gatcacctcg    180
gtggccgacg cggtggaaaa cgcgtcgttc gtcgtggtcg cggtgaaacc ggccgacgtc    240
gagtcggtga tgtccgagat cgcccgcgcc gccggccagg ccgagagcga caccgccgag    300
caggtgttcg tcacggtcgc cgccggggtc accatcggct acttcgaatc ccggctgccg    360
gccgggacac cggtggtgcg ggccatgccg aacgcggccg tgctggtcgg cgccggggtc    420
accgccctgg ccaagggccg cttcgtcacc gccccgcagc tcgagggcgt ctcggcgctg    480
ttcgactcgg tcgggggcgt gctgagcgtg ccggagagcc agatggacgc cgtcaccgcc    540
ctctccggct ccgggccggc gtatttcttc ctgctggtgg aggccctggt ggacgccggg    600
gtggccgcgg gcctgagccg cgaggtggcc gccgacctga ccgcccagac catggccggc    660
tcggcggcga tgctgctgga gcggatggac gccgatcggc gactgggcga ggcggagacg    720
cccgggctgc gggtggacgc caccgccacc cagctgcggg ccacggtgac ctccccgggc    780
ggcaccaccg cggccggcct gcgcgagctg gagcgggggg gcctgcgggc cgccgtcgac    840
gccgccgtcc aggccgccaa aatgcgctct gagcagctaa gaattacatc ggagtaa       897
```

<210> SEQ ID NO 39
<211> LENGTH: 298
<212> TYPE: PRT
<213> ORGANISM: Mycobacterium avium

<400> SEQUENCE: 39

```
Met Ser Ala Met Leu Ser Gly Met Ala Arg Ile Ala Ile Ile Gly Gly
1               5                   10                  15

Gly Ser Ile Gly Glu Ala Leu Leu Ser Gly Leu Leu Arg Ala Gly Arg
            20                  25                  30

Gln Val Lys Asp Leu Val Val Val Glu Arg Val Pro Glu Arg Ala Lys
        35                  40                  45

Tyr Leu Ala Asp Thr Tyr Ser Val Leu Ile Thr Ser Val Ala Asp Ala
    50                  55                  60

Val Glu Asn Ala Ser Phe Val Val Val Ala Val Lys Pro Ala Asp Val
65                  70                  75                  80

Glu Ser Val Met Ser Glu Ile Ala Arg Ala Ala Gly Gln Ala Glu Ser
                85                  90                  95

Asp Thr Ala Glu Gln Val Phe Val Thr Val Ala Ala Gly Val Thr Ile
            100                 105                 110

Gly Tyr Phe Glu Ser Arg Leu Pro Ala Gly Thr Pro Val Val Arg Ala
        115                 120                 125

Met Pro Asn Ala Ala Val Leu Val Gly Ala Gly Val Thr Ala Leu Ala
    130                 135                 140

Lys Gly Arg Phe Val Thr Ala Pro Gln Leu Glu Gly Val Ser Ala Leu
145                 150                 155                 160

Phe Asp Ser Val Gly Gly Val Leu Ser Val Pro Glu Ser Gln Met Asp
                165                 170                 175

Ala Val Thr Ala Leu Ser Gly Ser Gly Pro Ala Tyr Phe Phe Leu Leu
            180                 185                 190

Val Glu Ala Leu Val Asp Ala Gly Val Ala Ala Gly Leu Ser Arg Glu
        195                 200                 205

Val Ala Ala Asp Leu Thr Ala Gln Thr Met Ala Gly Ser Ala Ala Met
```

```
    210                 215                 220

Leu Leu Glu Arg Met Asp Ala Asp Arg Arg Leu Gly Glu Ala Glu Thr
225                 230                 235                 240

Pro Gly Leu Arg Val Asp Ala Thr Ala Thr Gln Leu Arg Ala Thr Val
                245                 250                 255

Thr Ser Pro Gly Gly Thr Thr Ala Ala Gly Leu Arg Glu Leu Glu Arg
            260                 265                 270

Gly Gly Leu Arg Ala Ala Val Asp Ala Ala Val Gln Ala Ala Lys Met
        275                 280                 285

Arg Ser Glu Gln Leu Arg Ile Thr Ser Glu
    290                 295
```

<210> SEQ ID NO 40
<211> LENGTH: 1104
<212> TYPE: DNA
<213> ORGANISM: Mycobacterium avium

<400> SEQUENCE: 40

```
tcagagctgc tgaccgaacc gcacccaacg cgcgagcagc tgttcggccg cgccggagtc      60
gatggcggcg ctggcgcggg ccagcccgtc ctcccaggcc ggcaaccatt cggcgcggct     120
ggataacccg gcgtgcgcca cgatcgcgcc ggcggcgttg aggacgacgg cgtcgcgcac     180
cgggccctgg ccgccggcca gcaccgcccg cacctccgcg gcgttggtct gcgcgtcacc     240
gcccaacaga tcgtcgagct cggcccgcgg gaaaccgaac ccggccggat cgaacgtcaa     300
ccggtccacc gtgccggcct gcacccgcca gatggtgctg gtcgtcgtgg tggtcaactc     360
gtcgagcccg tcgtcgccgt gcaccaccag cacactggag cgccgggcgg cgaacacccc     420
ggccatcacc tcggccagct cggcgaacgc gcagccgatc aatccggccc gcggtcgagc     480
cggattggta agcggcccaa gcagattgaa caccgtcggc acgccgatct cgcggcgcac     540
cgccgaggta tgccggtagg acgggtggaa cagcggcgcg aagcagaatc cgatgccgac     600
ttcggcgaca ctgcgcgcga cctgctcggg gcccaggtcg atccgtaccc cgagctcctc     660
gagcgtgtcc gcgccgcccg agagcgacga cgccgcgcgg ttgccgtgtt tgaccaccgg     720
tacccccgcg gccgcggcca cgatcgccgc catcgtggac aggttgaggg tgttgacgcc     780
gtcgccgccg gtgccgacga tgtcgacggt gtcgtcgcgg atcgcgccgg cggggaacgg     840
cagcgcgtgg ttcagcatca cctcggccag ctcgatgacc tcggccgagg tggggacctt     900
cacctgcatc gccaccgcga aggccgcgat ctgggccggg ctcgcctcgc cggtcatgat     960
ctggtccatg gcccaggccg cctgtccgcg ggccaggtcg tcaccgccgg tcagccgggc    1020
cagcacctgg cgccacgacg tcgccggccc accggagggc cgccgggctg cggaagccgc    1080
agacgactca gatgacaacg ccac                                           1104
```

<210> SEQ ID NO 41
<211> LENGTH: 367
<212> TYPE: PRT
<213> ORGANISM: Mycobacterium avium

<400> SEQUENCE: 41

```
Met Ala Leu Ser Ser Glu Ser Ser Ala Ala Ser Ala Ala Arg Arg Pro
1               5                   10                  15

Ser Gly Gly Pro Ala Thr Ser Trp Arg Gln Val Leu Ala Arg Leu Thr
            20                  25                  30

Gly Gly Asp Asp Leu Ala Arg Gly Gln Ala Ala Trp Ala Met Asp Gln
        35                  40                  45
```

```
Ile Met Thr Gly Glu Ala Ser Pro Ala Gln Ile Ala Ala Phe Ala Val
 50                  55                  60

Ala Met Gln Val Lys Val Pro Thr Ser Ala Glu Val Ile Glu Leu Ala
 65                  70                  75                  80

Glu Val Met Leu Asn His Ala Leu Pro Phe Pro Ala Gly Ala Ile Arg
                 85                  90                  95

Asp Asp Thr Val Asp Ile Val Gly Thr Gly Asp Gly Val Asn Thr
            100                 105                 110

Leu Asn Leu Ser Thr Met Ala Ala Ile Val Ala Ala Ala Gly Val
            115                 120                 125

Pro Val Val Lys His Gly Asn Arg Ala Ala Ser Leu Ser Gly Gly
        130                 135                 140

Ala Asp Thr Leu Glu Glu Leu Gly Val Arg Ile Asp Leu Gly Pro Glu
145                 150                 155                 160

Gln Val Ala Arg Ser Val Ala Glu Val Gly Ile Gly Phe Cys Phe Ala
                165                 170                 175

Pro Leu Phe His Pro Ser Tyr Arg His Thr Ser Ala Val Arg Arg Glu
                180                 185                 190

Ile Gly Val Pro Thr Val Phe Asn Leu Leu Gly Pro Leu Thr Asn Pro
                195                 200                 205

Ala Arg Pro Arg Ala Gly Leu Ile Gly Cys Ala Phe Ala Glu Leu Ala
        210                 215                 220

Glu Val Met Ala Gly Val Phe Ala Ala Arg Ser Ser Val Leu Val
225                 230                 235                 240

Val His Gly Asp Asp Gly Leu Asp Glu Leu Thr Thr Thr Thr Ser
                245                 250                 255

Thr Ile Trp Arg Val Gln Ala Gly Thr Val Asp Arg Leu Thr Phe Asp
        260                 265                 270

Pro Ala Gly Phe Gly Phe Pro Arg Ala Glu Leu Asp Asp Leu Leu Gly
        275                 280                 285

Gly Asp Ala Gln Thr Asn Ala Ala Glu Val Arg Ala Val Leu Ala Gly
        290                 295                 300

Gly Gln Gly Pro Val Arg Asp Ala Val Val Leu Asn Ala Ala Gly Ala
305                 310                 315                 320

Ile Val Ala His Ala Gly Leu Ser Ser Arg Ala Glu Trp Leu Pro Ala
                325                 330                 335

Trp Glu Asp Gly Leu Ala Arg Ala Ser Ala Ala Ile Asp Ser Gly Ala
                340                 345                 350

Ala Glu Gln Leu Leu Ala Arg Trp Val Arg Phe Gly Gln Gln Leu
        355                 360                 365

<210> SEQ ID NO 42
<211> LENGTH: 903
<212> TYPE: DNA
<213> ORGANISM: Mycobacterium avium

<400> SEQUENCE: 42
gtgtcgcgcg aaaatcgaag tcgcagaagg ctgatcggcg gcgcataccg aagcctgcgg      60
ctgctcggcg ccgtggccgc ggtggcgctg gcggccagcc cgttgacacc gcgcaccagc     120
cttgcggcag cggccattcc gcaaccgtcg cacatcgtga tcgtggtgga ggaaaaccgt     180
tccgagagcg gcatcatcgg caacaagtcg gcgcccttca tcaccgcgct ggccgcgtcc     240
ggcgccaaca tgacccagtc gttcgccgaa acccacccca gcgagcccaa ttacctggcg     300
```

```
ctgttcgccg gcaacacgtt cggggtgacc aaggacctgt gcccggtcaa cgccggcgcc    360
gcacccaacc tggggtccga attgctcgcc gccggttaca cattcgtcgg ctacgccgag    420
ggcctgccgt ccccgggctc accggtgtgt agtgcgggca agtacgcgcg aaaacatgtg    480
ccgtgggcca acttcaccaa cgtgccggcg gctagctcgc tgccgttctc ggcgttcccg    540
atgggcaact acgccagcct gccgacggtg tcgttcgtca tcccgaacaa cgacaacaac    600
atgcacgacg gctcgatcgc gcaggccgac tcctggctga accggcagct gtccggctac    660
gccaattggg cgctggccaa caacagcctg ctgatcgtca ccttcgacga ggacgacaac    720
tccaacgtcg gagccagccg caaccagatc cccacggtgt tctacggcgc ccacgtccgg    780
cccggcaact acgccgagca gatcaaccac tacaacgtgc ttgccaccct cgagcagatg    840
tacgggctgc caagacgggc tatgccgcc ggcgccgccc ccatcaccga catctggggc    900
tga                                                                  903

<210> SEQ ID NO 43
<211> LENGTH: 300
<212> TYPE: PRT
<213> ORGANISM: Mycobacterium avium

<400> SEQUENCE: 43

Met Ser Arg Glu Asn Arg Ser Arg Arg Leu Ile Gly Gly Ala Tyr
1               5                   10                  15

Arg Ser Leu Arg Leu Leu Gly Ala Val Ala Ala Val Ala Leu Ala Ala
            20                  25                  30

Ser Pro Leu Thr Pro Arg Thr Ser Leu Ala Ala Ala Ile Pro Gln
        35                  40                  45

Pro Ser His Ile Val Ile Val Val Glu Glu Asn Arg Ser Glu Ser Gly
    50                  55                  60

Ile Ile Gly Asn Lys Ser Ala Pro Phe Ile Thr Ala Leu Ala Ala Ser
65                  70                  75                  80

Gly Ala Asn Met Thr Gln Ser Phe Ala Glu Thr His Pro Ser Glu Pro
                85                  90                  95

Asn Tyr Leu Ala Leu Phe Ala Gly Asn Thr Phe Gly Val Thr Lys Asp
            100                 105                 110

Leu Cys Pro Val Asn Ala Gly Ala Pro Asn Leu Gly Ser Glu Leu
        115                 120                 125

Leu Ala Ala Gly Tyr Thr Phe Val Gly Tyr Ala Glu Gly Leu Pro Ser
    130                 135                 140

Pro Gly Ser Pro Val Cys Ser Ala Gly Lys Tyr Ala Arg Lys His Val
145                 150                 155                 160

Pro Trp Ala Asn Phe Thr Asn Val Pro Ala Ala Ser Ser Leu Pro Phe
                165                 170                 175

Ser Ala Phe Pro Met Gly Asn Tyr Ala Ser Leu Pro Thr Val Ser Phe
            180                 185                 190

Val Ile Pro Asn Asn Asp Asn Asn Met His Asp Gly Ser Ile Ala Gln
        195                 200                 205

Ala Asp Ser Trp Leu Asn Arg Gln Leu Ser Gly Tyr Ala Asn Trp Ala
    210                 215                 220

Leu Ala Asn Asn Ser Leu Leu Ile Val Thr Phe Asp Glu Asp Asp Asn
225                 230                 235                 240

Ser Asn Val Gly Ala Ser Arg Asn Gln Ile Pro Thr Val Phe Tyr Gly
                245                 250                 255

Ala His Val Arg Pro Gly Asn Tyr Ala Glu Gln Ile Asn His Tyr Asn
```

260                 265                 270
Val Leu Ala Thr Leu Glu Gln Met Tyr Gly Leu Pro Lys Thr Gly Tyr
            275                 280                 285

Ala Ala Gly Ala Ala Pro Ile Thr Asp Ile Trp Gly
        290                 295                 300

<210> SEQ ID NO 44
<211> LENGTH: 1334
<212> TYPE: DNA
<213> ORGANISM: Mycobacterium avium

<400> SEQUENCE: 44
ctacccgcgg tcgcgggcca gcaggtcggc cacggtttcg cggcggacca gttcccgggc       60
ccggccctcg ctgaccgcca ccagcggcgg gcgcccgacc atgttgtagt tcgacgccat      120
gctgtggtgg taggcgccgg tgcaggccac ggccagcagg tcacccgggc gcagatcggc      180
gggcagctcg acgtcgcggg cgatctcgtc gccggactcg cagtgccggc ccgccaccgt      240
gacccgctgc ttgaggccca gcggatgccg gttggccagc gcgacggcat accgcgcgcc      300
gtacagcgac acccgcgggt tgtcgctcat gccgccgtcg acggcgacga aggtccgccc      360
gccgccttgc gtcttcaccg agcacacccg gtacagggtc accccggccc gaccgctgat      420
cgcccggccc ggctccacca cgatctgcgg gcggggaaac cgctcggcgg cgcacgcctc      480
gtccagggcg tcctcgatca cgtcggccag ctggtcgagg ttcagctccg ggtcgccgga      540
cgcatacgga atggcatgtc ccccaccgat attcagctcg gtcaggatga cgccgtgccg      600
ggcccggata tcgccatcg cggcgatcat ccggcggatc gcctcgccgt acagggcggg      660
gtcggacacc tgcgagccga ggtggcagtg caggccgacc aggtcgagga tggggtgggc      720
cagcacccgg cgcaccgcgt cggccgcgtg gtcgccggcc aggtgaagc cgaacttctg      780
gtcgctgacg ccggtggtga cggcgcgatg cccgtggatg tcgatgtcgg gggtgacccg      840
gatgagcacc ggctggcggc gacgggccag gccggccaga tacgcgatct cgatggtcga      900
atccagcacg atgcggccca cccgacgcg caccgcctcg cgcagctcct cgggcgattt      960
cgcgttgccg tgcatgacga tgcgggccgg gtcgaccccg ccggcagcg cggtggccag     1020
ttcaccggcc gagcagacgt cgacgccgag gcgctcctcg cgggcccacc gggccaccgc     1080
ggtgctcagc agggacttgc cggcgtagac cacctcgacg ccgcgcagcg ccctgcggta     1140
ccggcgggcg cggcaccgga agtcggcttc gtcgacgacg taggccgggg tgccgaactc     1200
gtcggcgacg tcgcccagcg gcacgccgcc gacgcacagc cggccctcct cgtcgggatg     1260
ggcggtgacg ggccagatcg ccggatcgaa ccgtggggga gccgcgtgac ccagcgacgg     1320
caggatgtcc agca                                                     1334

<210> SEQ ID NO 45
<211> LENGTH: 444
<212> TYPE: PRT
<213> ORGANISM: Mycobacterium avium

<400> SEQUENCE: 45

Met Leu Asp Ile Leu Pro Ser Leu Gly His Ala Pro Pro Arg Phe
1               5                   10                  15

Asp Pro Ala Ile Trp Pro Val Thr Ala His Pro Asp Glu Glu Gly Arg
            20                  25                  30

Leu Cys Val Gly Gly Val Pro Leu Gly Asp Val Ala Asp Glu Phe Gly
        35                  40                  45

Thr Pro Ala Tyr Val Val Asp Glu Ala Asp Phe Arg Cys Arg Ala Arg
    50                  55                  60

Arg Tyr Arg Arg Ala Leu Arg Gly Val Glu Val Val Tyr Ala Gly Lys
 65                  70                  75                  80

Ser Leu Leu Ser Thr Ala Val Ala Arg Trp Ala Arg Glu Arg Leu
                 85                  90                  95

Gly Val Asp Val Cys Ser Ala Gly Glu Leu Ala Thr Ala Leu Ala Gly
                100                 105                 110

Gly Val Asp Pro Ala Arg Ile Val Met His Gly Asn Ala Lys Ser Pro
                115                 120                 125

Glu Glu Leu Arg Glu Ala Val Arg Val Gly Val Gly Arg Ile Val Leu
130                 135                 140

Asp Ser Thr Ile Glu Ile Ala Tyr Leu Ala Gly Leu Ala Arg Arg
145                 150                 155                 160

Gln Pro Val Leu Ile Arg Val Thr Pro Asp Ile Asp Ile His Gly His
                165                 170                 175

Arg Ala Val Thr Thr Gly Val Ser Asp Gln Lys Phe Gly Phe Thr Leu
                180                 185                 190

Ala Gly Asp His Ala Ala Asp Ala Val Arg Arg Val Leu Ala His Pro
                195                 200                 205

Ile Leu Asp Leu Val Gly Leu His Cys His Leu Gly Ser Gln Val Ser
210                 215                 220

Asp Pro Ala Leu Tyr Gly Glu Ala Ile Arg Arg Met Ile Ala Ala Met
225                 230                 235                 240

Ala Asp Ile Arg Ala Arg His Gly Val Ile Leu Thr Glu Leu Asn Ile
                245                 250                 255

Gly Gly Gly His Ala Ile Pro Tyr Ala Ser Gly Asp Pro Glu Leu Asn
                260                 265                 270

Leu Asp Gln Leu Ala Asp Val Ile Glu Asp Ala Leu Asp Glu Ala Cys
                275                 280                 285

Ala Ala Glu Arg Phe Pro Arg Pro Gln Ile Val Val Glu Pro Gly Arg
290                 295                 300

Ala Ile Ser Gly Arg Ala Gly Val Thr Leu Tyr Arg Val Cys Ser Val
305                 310                 315                 320

Lys Thr Gln Gly Gly Arg Thr Phe Val Ala Val Asp Gly Gly Met
                325                 330                 335

Ser Asp Asn Pro Arg Val Ser Leu Tyr Gly Ala Arg Tyr Ala Val Ala
                340                 345                 350

Leu Ala Asn Arg His Pro Leu Gly Leu Lys Gln Arg Val Thr Val Ala
                355                 360                 365

Gly Arg His Cys Glu Ser Gly Asp Glu Ile Ala Arg Asp Val Glu Leu
                370                 375                 380

Pro Ala Asp Leu Arg Pro Gly Asp Leu Leu Ala Val Ala Cys Thr Gly
385                 390                 395                 400

Ala Tyr His His Ser Met Ala Ser Asn Tyr Asn Met Val Gly Arg Pro
                405                 410                 415

Pro Leu Val Ala Val Ser Glu Gly Arg Ala Arg Glu Leu Val Arg Arg
                420                 425                 430

Glu Thr Val Ala Asp Leu Leu Ala Arg Asp Arg Gly
                435                 440

<210> SEQ ID NO 46
<211> LENGTH: 603
<212> TYPE: DNA

<213> ORGANISM: Mycobacterium avium

<400> SEQUENCE: 46

```
tcacgcgacg ggcgaagtgc gcggtttcca atcgggatac gtcgcttcgt aggattcgat      60
tctgtcgagt ttccgcagcg taagggctat atcgtcgagc ccttcgagta gtcgccacgc     120
ggtgtggtcg tcaatcttga acggcagcac cgtcgttccc gcggtgatat ttcgatcttg     180
aagattggca gtgatttcca agccggggct ctgctcgatg agcttccaga gcagctccac     240
cccgtcctgg gaaacttcgg ccgccagcag acccgccttg ccggcgttgc cccggaaaat     300
gtcgccgaat cgagacgaga tgaccacccg gaacccgtag tccatcagtg cccacaccgc     360
gtgctcgcgc gacgaccccg tcccgaaatc cggtccggcg actaggactg agccacggtc     420
aaagggctg aggttgagca cgaatgacgg atccgaccgc cagctggcga acaagccgtc      480
ctcgaaaccg gttcgggtta cgcgcttcaa atacaccgcc ggaatgatct ggtcggtgtc     540
gacattggag cgccgcagcg gcacaccgat gccggtgtgg gtgtgaaatg cttccatgct     600
cat                                                                  603
```

<210> SEQ ID NO 47
<211> LENGTH: 200
<212> TYPE: PRT
<213> ORGANISM: Mycobacterium avium

<400> SEQUENCE: 47

```
Met Ser Met Glu Ala Phe His Thr His Thr Gly Ile Gly Val Pro Leu
1               5                   10                  15

Arg Arg Ser Asn Val Asp Thr Asp Gln Ile Ile Pro Ala Val Tyr Leu
            20                  25                  30

Lys Arg Val Thr Arg Thr Gly Phe Glu Asp Gly Leu Phe Ala Ser Trp
        35                  40                  45

Arg Ser Asp Pro Ser Phe Val Leu Asn Leu Ser Pro Phe Asp Arg Gly
    50                  55                  60

Ser Val Leu Val Ala Gly Pro Asp Phe Gly Thr Gly Ser Ser Arg Glu
65                  70                  75                  80

His Ala Val Trp Ala Leu Met Asp Tyr Gly Phe Arg Val Ile Ser
                85                  90                  95

Ser Arg Phe Gly Asp Ile Phe Arg Gly Asn Ala Gly Lys Ala Gly Leu
            100                 105                 110

Leu Ala Ala Glu Val Ser Gln Asp Gly Val Glu Leu Leu Trp Lys Leu
        115                 120                 125

Ile Glu Gln Ser Pro Gly Leu Glu Ile Thr Ala Leu Asn Leu Gln Asp Arg
    130                 135                 140

Asn Ile Thr Ala Gly Thr Thr Val Leu Pro Phe Lys Ile Asp Asp His
145                 150                 155                 160

Thr Ala Trp Arg Leu Leu Glu Gly Leu Asp Asp Ile Ala Leu Thr Leu
                165                 170                 175

Arg Lys Leu Asp Arg Ile Glu Ser Tyr Glu Ala Thr Tyr Pro Asp Trp
            180                 185                 190

Lys Pro Arg Thr Ser Pro Val Ala
        195                 200
```

<210> SEQ ID NO 48
<211> LENGTH: 1431
<212> TYPE: DNA
<213> ORGANISM: Mycobacterium avium -continued

<400> SEQUENCE: 48

```
tcagtccaaa tcggccggag cggacaatgt gccgcgcacc gccgtggccg cggcgacggc      60
cggagacacc aaatgcgtgc ggccgccttt gccctggcgc ccttcgaagt tgcggttcga     120
ggtcgccgcg caccgctccc ccggcgccag ctgatcggga ttcattccca aacacatcga     180
gcagcccgcc tgccgccatt cggcgcccgc ggcggtgaaa acctcgccca gcccttcggc     240
ttcggcctgc gcgcgcaccc gcatcgagcc gggcaccacg agcatccgca cccccggcgc     300
gaccttgcgg ccgcgcagca cgtcggcgac gacccgcaga tcctcgatac gaccgttggt     360
acaagagccg acgaacaccg cgtcgaccgc gatgtcgcgc atcggcgtgc ccggtcgaag     420
gtccatgtat gccaacgctt tctcggcggc ctgacgctcg gcatcgtcgg tcatcagttc     480
gggatccggt accgcggcag ccaacggcac gccctgaccc gggtttgtgc cccacgtcac     540
gaacgggctc agcgacgcgg catccagata gacctcggtg tcgaacaccg cgccgggatc     600
ggtgcgcagc tgctgccaat agcgcatggc cgcatcccat tgcgcgccct tgggggcgtg     660
cgggcggtcc cgcaggaact cgtaggtggt gtcgtcggga gcgatcatcc ccgctcgggc     720
accggcctcg atgctcatgt tgcacacggt catccggcct tccatcgaca gcgattcgat     780
ggcgctgccg cggtattcga tgacgtgccc ctgcccgccg ccggtgccga tcttggcgat     840
cagcgccagg atgatgtcct tggccgtcac gccggccggc aactcgccgt cgacgttgac     900
cgccatcgtc ttgaacggcc gcagcggcaa cgtctgggtg gccagcacgt gctcgacctc     960
cgaggtgcca attcccatgg ccagtgcgcc gaatgcgccg tgcgtcgagg tgtgactatc    1020
cccacacacc accgtcattc ccggttgggt caggcccagc tgcggcccga cgacatgcac    1080
gatgccctgc tccgcgtcgc ccatcgggta cagccggacg ccgaattcgg cacaatttcg    1140
gcgcaatgtc tcgacctggg tgcgcgacac cgggtcggcg atcggcttgt cgatgtcgac    1200
ggtgggcacg ttgtggtcct cggtggccag cgtcagatcg ggccgccgca ccggccggcc    1260
ggccagccgc aggccgtcga acgcctgcgg gctggtgacc tcgtgcacca ggtgcagatc    1320
gatgtagatc aggtccggct cgttggcccc gccggacacc acaacgtggt cgtcccagac    1380
tttttcggcc agcgtgcgcg gcgtggccgt cgtccccgtg tcgattccca t             1431
```

<210> SEQ ID NO 49
<211> LENGTH: 476
<212> TYPE: PRT
<213> ORGANISM: Mycobacterium avium

<400> SEQUENCE: 49

```
Met Gly Ile Asp Thr Gly Thr Thr Ala Thr Pro Arg Thr Leu Ala Glu
1               5                   10                  15

Lys Val Trp Asp Asp His Val Val Val Ser Gly Gly Ala Asn Glu Pro
            20                  25                  30

Asp Leu Ile Tyr Ile Asp Leu His Leu Val His Glu Val Thr Ser Pro
        35                  40                  45

Gln Ala Phe Asp Gly Leu Arg Leu Ala Gly Arg Pro Val Arg Arg Pro
    50                  55                  60

Asp Leu Thr Leu Ala Thr Glu Asp His Asn Val Pro Thr Val Asp Ile
65                  70                  75                  80

Asp Lys Pro Ile Ala Asp Pro Val Ser Arg Thr Gln Val Glu Thr Leu
                85                  90                  95

Arg Arg Asn Cys Ala Glu Phe Gly Val Arg Leu Tyr Pro Met Gly Asp
            100                 105                 110
```

-continued

```
Ala Glu Gln Gly Ile Val His Val Val Gly Pro Gln Leu Gly Leu Thr
        115                 120                 125
Gln Pro Gly Met Thr Val Val Cys Gly Asp Ser His Thr Ser Thr His
        130                 135                 140
Gly Ala Phe Gly Ala Leu Ala Met Gly Ile Gly Thr Ser Glu Val Glu
145                 150                 155                 160
His Val Leu Ala Thr Gln Thr Leu Pro Leu Arg Pro Phe Lys Thr Met
                165                 170                 175
Ala Val Asn Val Asp Gly Glu Leu Pro Ala Gly Val Thr Ala Lys Asp
                180                 185                 190
Ile Ile Leu Ala Leu Ile Ala Lys Ile Gly Thr Gly Gly Gly Gln Gly
        195                 200                 205
His Val Ile Glu Tyr Arg Gly Ser Ala Ile Glu Ser Leu Ser Met Glu
        210                 215                 220
Gly Arg Met Thr Val Cys Asn Met Ser Ile Glu Ala Gly Ala Arg Ala
225                 230                 235                 240
Gly Met Ile Ala Pro Asp Asp Thr Thr Tyr Glu Phe Leu Arg Asp Arg
                245                 250                 255
Pro His Ala Pro Lys Gly Ala Gln Trp Asp Ala Ala Met Arg Tyr Trp
                260                 265                 270
Gln Gln Leu Arg Thr Asp Pro Gly Ala Val Phe Asp Thr Glu Val Tyr
        275                 280                 285
Leu Asp Ala Ala Ser Leu Ser Pro Phe Val Thr Trp Gly Thr Asn Pro
290                 295                 300
Gly Gln Gly Val Pro Leu Ala Ala Val Pro Asp Pro Glu Leu Met
305                 310                 315                 320
Thr Asp Asp Ala Glu Arg Gln Ala Ala Glu Lys Ala Leu Ala Tyr Met
                325                 330                 335
Asp Leu Arg Pro Gly Thr Pro Met Arg Asp Ile Ala Val Asp Ala Val
                340                 345                 350
Phe Val Gly Ser Cys Thr Asn Gly Arg Ile Glu Asp Leu Arg Val Val
        355                 360                 365
Ala Asp Val Leu Arg Gly Arg Lys Val Ala Pro Gly Val Arg Met Leu
370                 375                 380
Val Val Pro Gly Ser Met Arg Val Arg Ala Gln Ala Glu Ala Glu Gly
385                 390                 395                 400
Leu Gly Glu Val Phe Thr Ala Ala Gly Ala Glu Trp Arg Gln Ala Gly
                405                 410                 415
Cys Ser Met Cys Leu Gly Met Asn Pro Asp Gln Leu Ala Pro Gly Glu
                420                 425                 430
Arg Cys Ala Ala Thr Ser Asn Arg Asn Phe Glu Gly Arg Gln Gly Lys
        435                 440                 445
Gly Gly Arg Thr His Leu Val Ser Pro Ala Val Ala Ala Ala Thr Ala
        450                 455                 460
Val Arg Gly Thr Leu Ser Ala Pro Ala Asp Leu Asp
465                 470                 475
```